United States Patent

Sakiyama et al.

Patent Number: 5,140,265
Date of Patent: Aug. 18, 1992

[54] EDDY CURRENT FLAW DETECTING ENDOSCOPE APPARATUS WHICH PRODUCES SIGNALS WHICH CONTROL OTHER DEVICES

[75] Inventors: Katsunori Sakiyama, Hachioji; Yoshikazu Tojo, Fussa; Yasundo Tanaka, Urawa; Morihide Mizumoto, Hachioji; Minoru Okada, Sagamihara; Masanao Murata, Tokorozawa; Atsushi Miyazaki, Hachioji; Takeaki Nakamura, Hino; Hiromasa Suzuki, Akishima, all of Japan

[73] Assignee: Olympus Optical Co., Ltd, Tokyo, Japan

[21] Appl. No.: 558,534

[22] Filed: Jul. 27, 1990

[30] Foreign Application Priority Data

Dec. 20, 1989 [JP] Japan .................. 1-332262
Dec. 20, 1989 [JP] Japan .................. 1-332263
Feb. 2, 1990 [JP] Japan .................. 2-27843
Feb. 15, 1990 [JP] Japan .................. 2-35242

[51] Int. Cl.$^5$ ............... G01N 27/90; G01R 33/12; H04N 7/18
[52] U.S. Cl. .................. 324/220; 358/98; 324/226; 324/237; 324/240
[58] Field of Search ................ 324/219–221, 324/226–228; 358/98, 100

[56] References Cited

U.S. PATENT DOCUMENTS

| | | | |
|---|---|---|---|
| 4,139,822 | 2/1979 | Urich et al. | 324/219 |
| 4,178,875 | 12/1979 | Moschetti | 324/220 X |
| 4,372,658 | 2/1983 | O'Connor et al. | 324/220 X |
| 4,393,598 | 7/1983 | Powell et al. | 324/221 X |
| 4,412,177 | 10/1983 | Petrini et al. | 324/219 X |
| 4,608,534 | 8/1986 | Cecco et al. | 324/220 X |
| 4,675,604 | 6/1987 | Moyer et al. | 324/227 X |
| 4,856,337 | 8/1989 | Metala et al. | 324/226 X |
| 4,866,514 | 9/1989 | Hibino et al. | 358/98 |

FOREIGN PATENT DOCUMENTS

| | | |
|---|---|---|
| 56-157670 | 4/1980 | Japan . |
| 60-33313 | 3/1985 | Japan . |
| 61-38558 | 2/1986 | Japan . |
| 61-155754 | 7/1986 | Japan . |
| 63-90758 | 4/1988 | Japan . |

Primary Examiner—Kenneth A. Wieder
Assistant Examiner—Warren S. Edmonds
Attorney, Agent, or Firm—Armstrong & Kubovcik

[57] ABSTRACT

An eddy current flaw detecting endoscope apparatus has an endoscope having an elongate insertable part and an objective optical system provided on the tip side of the insertable part. A flaw detecting device is provided on the tip side of the endoscope. A signal processing device processes a signal for the flaw detecting device. An eddy current flaw detecting apparatus detects a flaw in an object to be inspected and generates a flaw detecting signal. A controlling device generates a control signal controlling a controlled device with a flaw detecting signal of the eddy current flaw detecting apparatus.

30 Claims, 23 Drawing Sheets

FIG.2
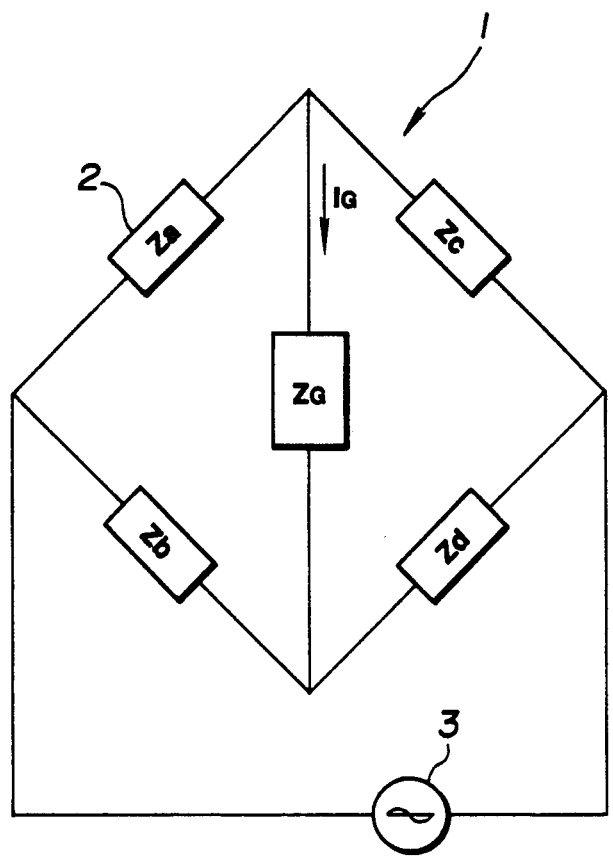
FIG.3 FIG.4
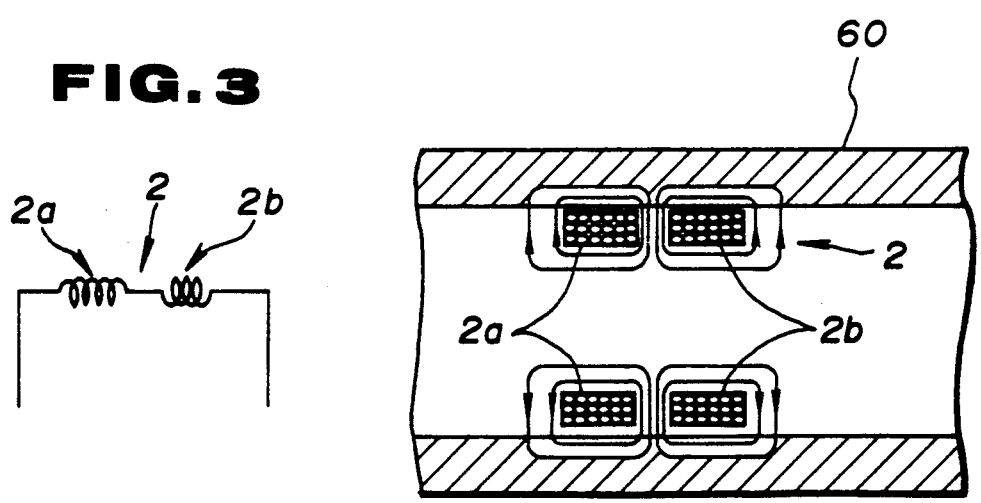

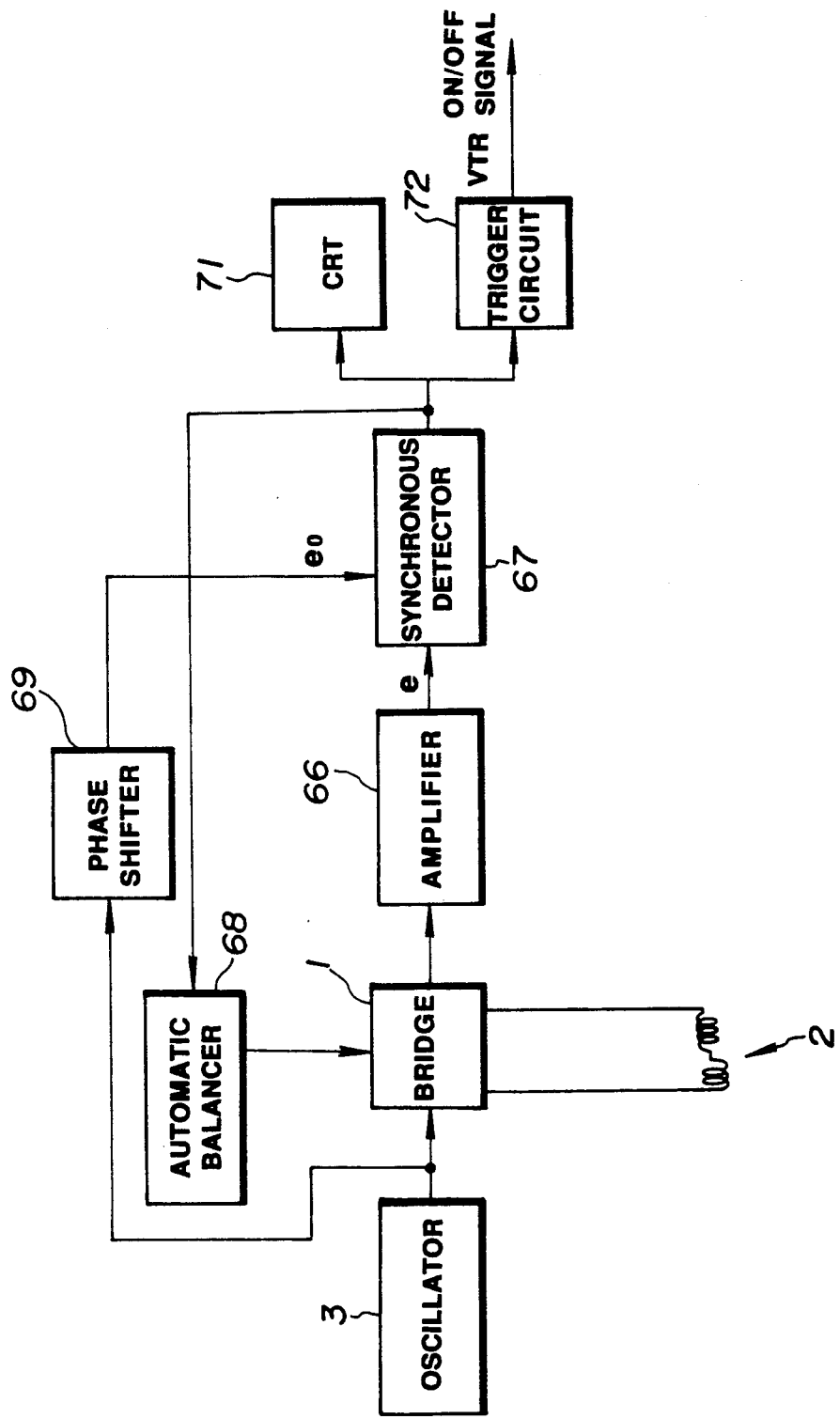

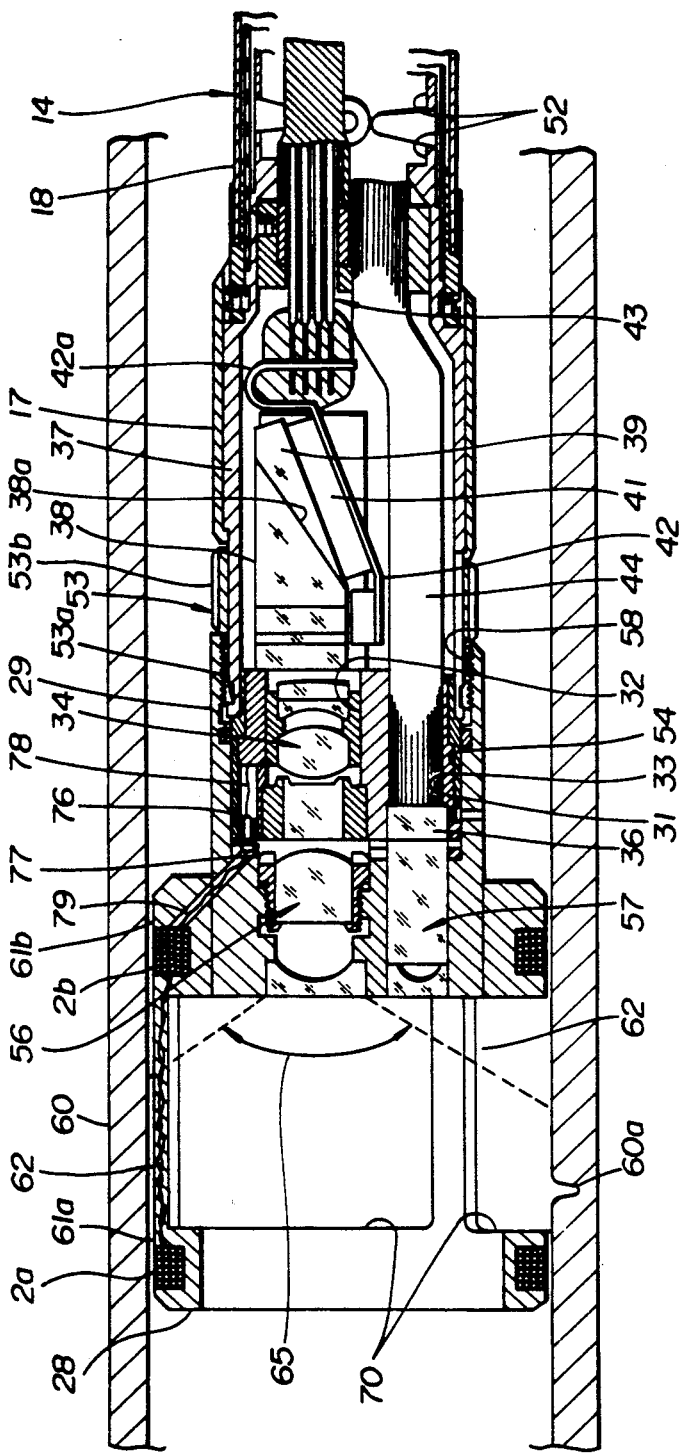
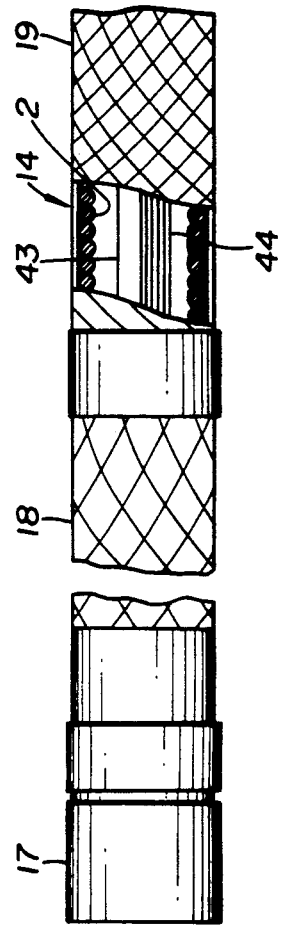
FIG.12
FIG.13

FIG.18(A)   FIG.18(B)   FIG.18(C)
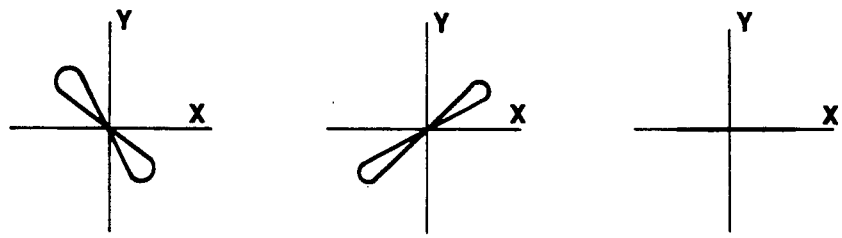
FIG.19                    FIG.21
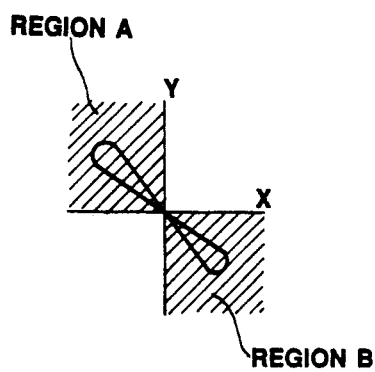  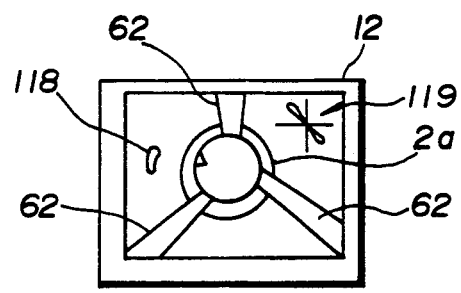
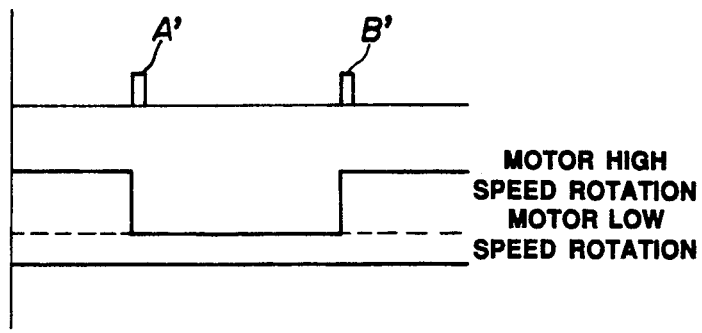

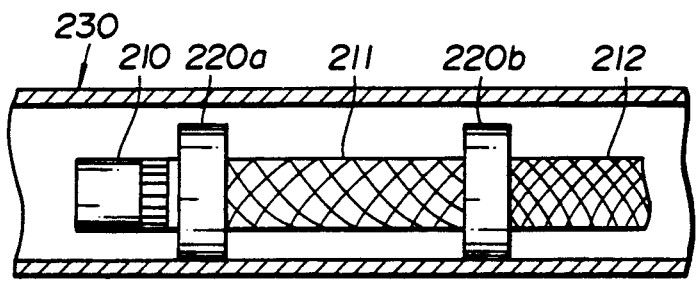
FIG. 25(A)
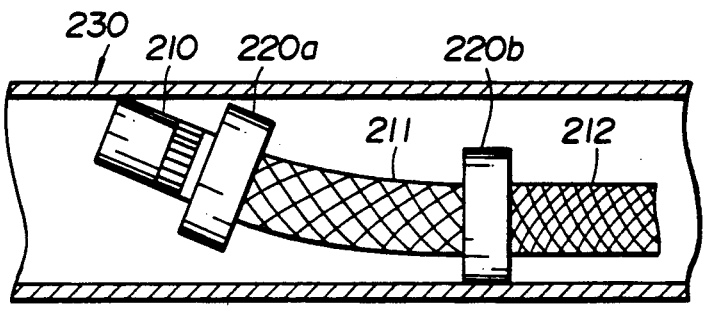
FIG. 25(B)
FIG. 26
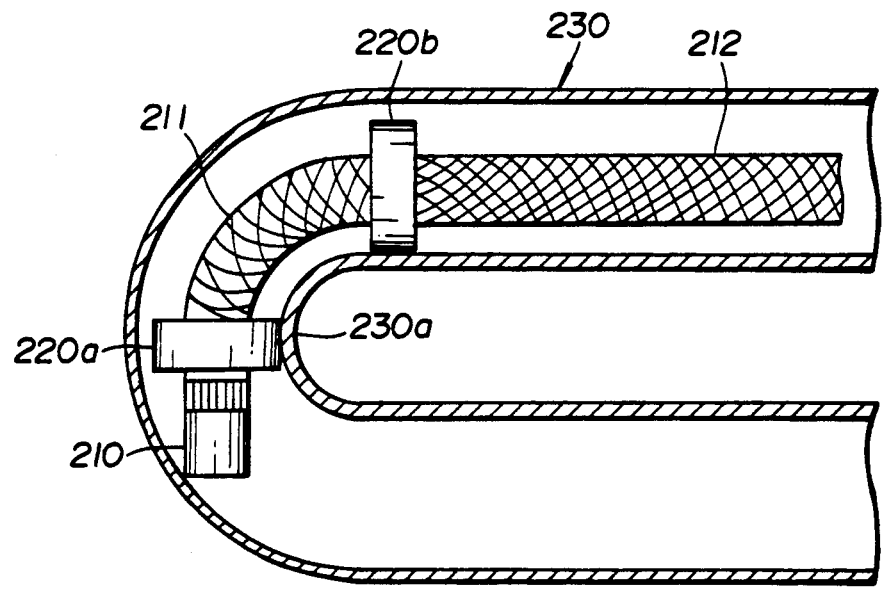

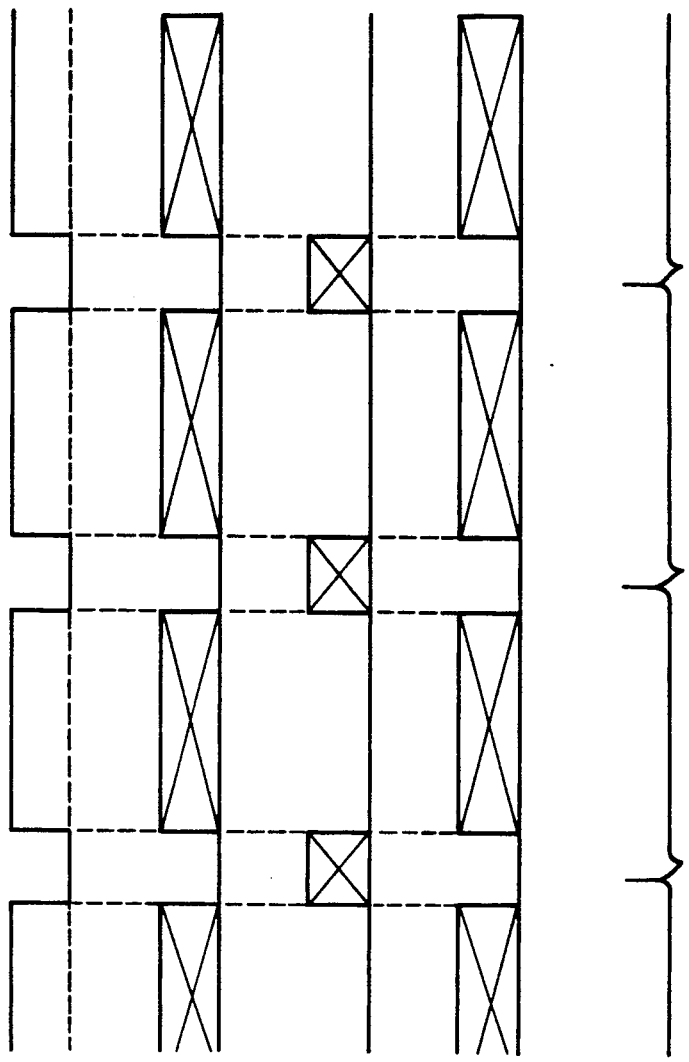

EDDY CURRENT FLAW DETECTING ENDOSCOPE APPARATUS WHICH PRODUCES SIGNALS WHICH CONTROL OTHER DEVICES

BACKGROUND OF THE INVENTION

1. Field of the Invention

This invention relates to an eddy current flaw detecting endoscope apparatus whereby a flaw of a part of an object to be inspected is detected without invading the object and an observed image of the above mentioned object is obtained.

2. Related Art Statement

Recently there is extensively used an endoscope (scope or fiberscope) whereby organs within a body cavity can be diagnosed or inspected by inserting an elongate insertable part into the body cavity. For not only medical but also industrial uses, such an endoscope is used to observe and inspect an object within a tube of a boiler, turbine, engine, machine or chemical plant or within a machine.

For the above described industrial uses, an eddy current flaw detecting apparatus or endoscope apparatus is practically used to inspect and observe a flaw such as a scratch or corrosion within a pipe line.

With the above mentioned eddy current flaw detecting apparatus, an eddy current is induced into an inspected object (dielectric) by an alternating magnetic field of an eddy current detecting coil moved within object such as a pipe line and a phenomenon that the value of this eddy current varies with a scratch or corrosion existing within the inspected object is taken as an impedance variation of the above mentioned coil so that the size and position of such flaw as the above mentioned scratch or corrosion may be detected at a high speed without invading the object.

With the above mentioned endoscope apparatus, an insertable part provided at the tip with an observing window is inserted into an object to be inspected and an object image obtained from the observing window is optically observed. There are used also various kinds of endoscope apparatus for electrically observing an object image obtained from an observing window by using an imaging means such as a charge coupled device (CCD).

An apparatus in which an eddy current flaw detecting apparatus and endoscope apparatus are combined with each other is shown in the publications, for example, of Japanese Patent Applications Laid Open Nos. 38558/1986, 155754/1986 and 90758/1988 and Japanese Utility Model Applications Laid Open Nos. 157670/1981 and 33313/1985.

In the publication of the above mentioned Japanese Patent Application Laid Open No. 38558/1986, an eddy current flaw detecting coil is provided near a scope head of an endoscope (fiberscope). In the publication of the above mentioned Japanese Patent Application Laid Open No. 155754/1986, at least two of a a) head provided with a sighting camera, b) head provided with an eddy current flaw detecting probe and c) head provided with an ultrasonic flaw detecting probe, are connected to a connecting member at the tip so as to detect a flaw by rotating each head. In the publication of the above mentioned Japanese Patent Application Laid Open No. 90758/1988, an eddy current flaw detecting means and an image guide by which a pipe can be observed over the entire inner peripheral surface are provided in the insertable part at the tip. In the publication of the above mentioned Japanese Utility Model Application Laid Open No. 157670/1981, an eddy current flaw detecting coil is removably provided in a bore scope at the tip. In the publication of the above mentioned Japanese Utility Model Application Laid Open No. 33313/1985, an optical fiber tip part of an endoscope (fiberscope) is arranged in the head part inserted through a pipe and an optical system for directing the optical axis of the above mentioned optical fiber to the pipe wall and an eddy current flaw detecting inspecting coil are provided so that an object image may be transmitted by the optical fiber from the tip of the endoscope to the base side and may be optically observed. According to such apparatus, a flaw part within a pipe can be detected by an eddy current or ultrasonic wave and can be visibly observed.

However, in the arts shown in the publications of the above mentioned Japanese Patent Application Laid Open Nos. 38558/1986, 155754/1986 and 90758/1988 and Japanese Utility Model Application Laid Open No. 90785/1988, no control signal will be input and output between a video tape recorder recording an endoscope image and eddy current flaw detecting apparatus and therefore the picture recording by the video tape recorder (abbreviated as the VTR hereinafter) and the inspection by the eddy current flaw detecting apparatus has been made without any relation. Also, in case only a flaw part is to be recorded, whenever a flaw is detected by the eddy current flaw detecting apparatus, the VTR will have to be switched on/off by a switch or the like and the on/off operation is a problem.

In the art shown in the publication of the above mentioned Japanese Utility Model Application Laid Open No. 33313/1985, data such as the size of the flaw detected from the eddy current flaw detecting apparatus will be recorded in the VTR as superimposed on the endoscope image as video signals. However, in case the image of the flaw obtained from the endoscope apparatus and data such as the size of the flaw obtained from the eddy current flaw detecting apparatus are to be recorded in the VTR, the VTR will have to be always inputting the video signal from the eddy current flaw detecting apparatus and recording the endoscope image and therefore the endoscope image in which no flaw is produced, that is, which is not required to be inspected will be recorded and the video tape will be wasted.

The same as in the art in the publication of the above mentioned Japanese Patent Application Laid Open No. 38558/1986, in case only the flaw part is to be recorded, the VTR will have to be switched on/off by a switch or the like, the on/off operation will be a problem and the inspecting time will become long.

Also, in order to accurately obtain the depth or position of the flaw, for example, in case the insertable part is inserted or pulled, the insertable part will have to be kept stable within the object lest a movement should be produced in the flaw position of the flaw detection sensing member by the vibration of the insertable part.

In case only one eddy current flaw detecting coil or only one set not independent as shown in the publications of the above mentioned Japanese Utility Model Application Laid Open No. 33313/1985 and Japanese Patent Application Laid Open No. 90758/1988 is provided in the tip part of an endoscope, the inspecting time will become long.

In a flaw detecting endoscope apparatus using a solid state imaging device, an imaging signal from the solid state imaging device and an eddy current flaw detecting electric signal will interfere with each other, the image will be disturbed or a flaw or the like will be detected erroneously by a pseudo signal.

OBJECTS AND SUMMARY OF THE INVENTION

An object of the present invention is to provide an eddy current flaw detecting endoscope apparatus whereby an inspection can be made efficiently by reducing the inspecting time.

Another object of the present invention is to provide an eddy current flaw detecting endoscope apparatus whereby, in case only a picture required for an inspection is to be recorded, it can be recorded without making an operation for the recording.

Further, another object of the present invention is to provide an eddy current flaw detecting endoscope apparatus whereby an insertable part is stabilized within an object body and at least either of the size and position of a flaw part can be accurately obtained.

Another object of the present invention is to provide an eddy current flaw detecting endoscope apparatus whereby a plurality of parts to be inspected can be simultaneously inspected.

Another object of the present invention is to provide an eddy current flaw detecting endoscope apparatus whereby an endoscope observed image and an eddy current flaw detecting signal will not interfere with each other.

An eddy current flaw detecting endoscope apparatus of the present invention comprises an endoscope having an elongate insertable part and an objective optical system provided on the tip side of the above mentioned insertable part. An imaging device photoelectrically converts an optical image based on the above mentioned objective optical system. A video signal processing apparatus processes a signal for the above mentioned imaging device to convert it to a standard video signal. An eddy current flaw detecting apparatus having at least one flaw detecting device provided in the above mentioned insertable part. A signal processing device processes a signal for the above mentioned flaw detecting device, detects a flaw in an inspected body and generates a flaw detecting signal. A controlling device times the above mentioned video signal processing apparatus and eddy current flaw detecting apparatus.

Further, the eddy current flaw detecting endoscope apparatus of the present invention comprises, for example, a plurality of flaw detecting devices or the above mentioned flaw detecting device and pseudo member at predetermined intervals in the above mentioned insertable part.

The eddy current flaw detecting endoscope apparatus of the present invention comprises, for example, a plurality of flaw detecting devices for detecting flaws independently of each other in the above mentioned insertable part.

The other features and advantages of the present invention will become apparent enough with the following explanation.

BRIEF DESCRIPTION OF THE DRAWINGS

FIGS. 1 to 11 relate to the first embodiment of the present invention.

FIG. 1 is a general explanatory view of an endoscope apparatus.

FIG. 2 is a bridge circuit diagram for explaining the principle of an eddy current flaw detecting apparatus.

FIG. 3 is an explanatory view of coils.

FIG. 4 is an explanatory view of magnetic fluxes generated by the eddy current flaw detecting apparatus.

FIG. 6 is an explanatory diagram of an output signal of an eddy current flaw detecting coil.

FIG. 7 is a sectioned view of a tip part of an endoscope.

FIG. 8 is a magnified view of a tip part of a connector.

FIG. 9 is a perspective view of a C-ring provided on the connector.

FIG. 10 is a block diagram of an eddy current flaw detecting apparatus.

FIG. 12 is a sectioned view of an endoscope tip part relating to the second embodiment of the present invention.

FIG. 13 is a partial sectioned view of an endoscope insertable part relating to the third embodiment of the present invention.

FIG. 14 is a sectioned view of an eddy current flaw detecting probe for inspecting the inside wall of a small diameter pipe.

FIG. 15 is a sectioned view of an eddy current flaw detecting probe for inspecting the inside wall of a large diameter pipe.

FIGS. 16 to 21 relate to the fifth embodiment of the present invention.

FIG. 16 is a block diagram for explaining the formation of an endoscope apparatus.

FIG. 17 is a block diagram for explaining the circuit formation of the endoscope apparatus.

FIGS. 18(A) to (C) are explanatory views of vector patterns.

FIG. 19 is an explanatory view of a phase analysis.

FIGS. 20(A) and (B) are explanatory views of the operation of a CPU.

FIG. 21 is an explanatory view of a monitor image.

FIGS. 23 to 26 relate to the seventh embodiment of the present invention.

FIG. 25 is an explanatory view of a bendable part of an endoscope.

FIG. 24 is a formation view of an endoscope apparatus.

FIGS. 25(A) and (B) and FIG. 26 are explanatory views of a tip part of an endoscope as inserted into a body to be inspected.

FIG. 29 is a sectioned view of a tip part of an insertable part of an endoscope.

FIG. 30 is a side view showing the whole of an endoscope apparatus.

FIG. 31 is a block diagram showing the formation of an eddy current flaw detecting means.

FIG. 32 is a circuit diagram showing an eddy current flaw detecting bridge.

FIGS. 33 to 35 relate to the 11th embodiment of the present invention.

FIG. 33 is a formation view of a flaw detecting endoscope apparatus.

FIG. 34 is an explanatory view of a tip part of a flaw detecting endoscope.

FIGS. 35(A) to (B) are explanatory views showing timings of imaging and flaw detecting signals.

DETAILED DESCRIPTION OF THE PREFERRED EMBODIMENTS

Figure 1:
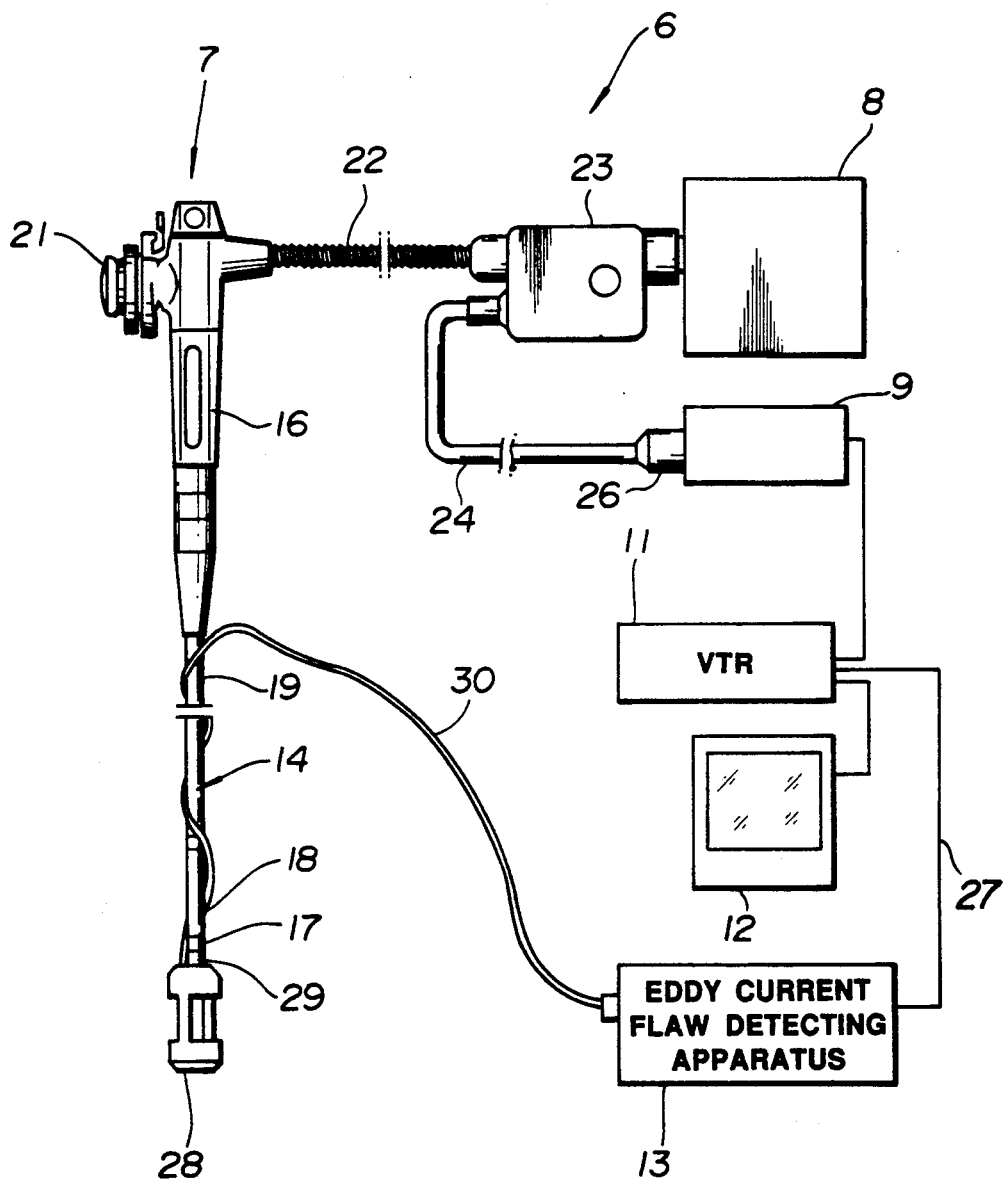

In FIGS. 1 to 11 is shown the first embodiment of the present invention.

First of all, the principle of an eddy current flaw detecting apparatus shall be explained.

In the eddy current flaw detecting apparatus, a flaw part is detected by the impedance variation of a coil. The impedance is detected by a bridge circuit 1 connected to an oscillator 3 shown in FIG. 2. A coil 2 has an impedance Za so that, when an electric current is made to flow by the above mentioned oscillator 3, an alternating magnetic field will be generated in the coil 2 and an eddy current will be generated in an object (magnetic object) to be inspected. Usually, in this state, the product of the impedances Za and Zd and the product of the impedances Zc and Zb of the bridge circuit 1 are equal to each other and the above mentioned bridge 1 is balanced. When there is a flaw part in the object, the value of the eddy current will vary, the impedance Za of the coil 2 will vary, thereby the balance of the bridge circuit 1 will be broken, a current (IG) will flow to an impedance ZG and a voltage will be produced at both ends of the impedance ZG. The flaw part in the object can be detected by the voltage produced at both ends of this impedance ZG.

FIGS. 3 and 4 show an example of the formation of the above mentioned coil 2. The above mentioned coil 2 is formed of 2b different from each other in the winding direction coils 2a and so as to generate magnetic fluxes in the directions different from each other to thereby remove noise produced by vibrations and the like.

Figure 5A:
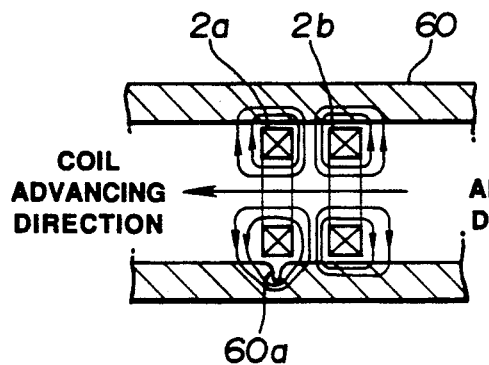
FIGS. 5(A) and (B) are explanatory views of the operation of the eddy current flaw detecting apparatus.
Figure 5B:
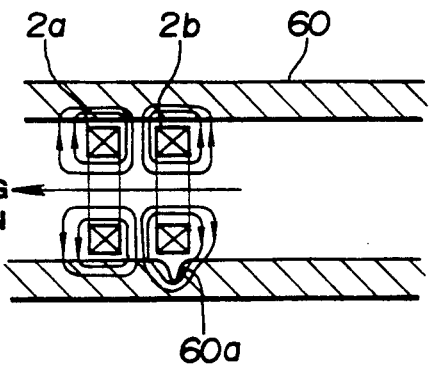
Figure 6:
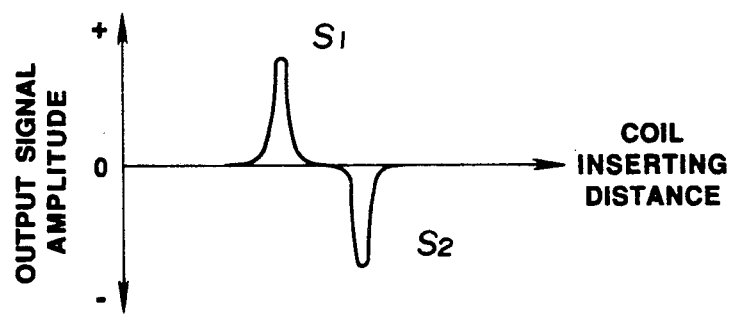

FIGS. 5(A), 5(B) and 6 are to explain an output signal in case the above mentioned coil 2 detects a flaw 60a in a pipe 60. In FIG. 5(A), when the coil 2 is advanced in the direction indicated by the arrow and the coil 2a reaches the flaw 60a, a signal S1 of an amplitude as is shown in FIG. 6 will be output. When the coil 2 is further advanced, the coil 2b on the rear end side will reach the flaw 60a and a signal S2 of a polarity opposite to that of the signal S1 will be output. The amplitudes by the vibrations or the like to which the above mentioned coils 2a and 2b are subjected in the same manner will be canceled with each other because the signals S1 and S2 are of reverse characteristics.

The formation of this embodiment shall be explained in the following.

As shown in FIG. 1, an endoscope apparatus 6 comprises an endoscope 7, a light source apparatus 8 for feeding an illuminating light to the above mentioned endoscope 7, a camera controlling unit (abbreviated as a CCU hereinafter) 9 provided with a video signal processing circuit, a video tape recorder (abbreviated as a VTR hereinafter) 11 recording an image, a monitor 12 displaying an endoscope image and an eddy current flaw detecting apparatus 13.

The above mentioned endoscope 7 is provided with an insertable part 14 and an operating part 16 connected to the insertable part 14 at the rear end. The above mentioned insertable part 14 is provided with a tip part 17, bendable part 18 and flexible tube part 19 in the order mentioned from the tip side. The above mentioned operating part 16 is connected to the above mentioned flexible tube part 19 at the rear end, is provided with a bending operation knob 21 which can operate to bend the bendable part 18, for example, in the vertical/horizontal direction and further has a universal cord 22 extended cut on the side. A light source connector 23 is provided at the rear end of the above mentioned universal cord 22 so as to be removably connected to the above mentioned light source apparatus 8. A signal universal cord 24 is extended out of the above mentioned light source connector 23. A signal connector 26 provided at the rear end of the above mentioned signal universal cord 24 is removably connected to the above mentioned CCU 9.

The above mentioned VTR 11 car record a video signal output out of the above mentioned CCU 9. The above mentioned VTR 11 is connected to the above mentioned monitor 12 and eddy current flaw detecting apparatus 13. A video signal for displaying an endoscope image on a picture is to be input into the above mentioned monitor 12 from the above mentioned VTR 11 and a recording on/off signal from the above mentioned eddy current flaw detecting apparatus 13 is to be input into the above mentioned VTR 11 through a VTR remote control cable 27.

The above mentioned tip part 17 is provided removably with an optical adapter 29 which is provided removably with an eddy current flaw detecting probe 28 connected to the above mentioned eddy current flaw detecting apparatus 13 through a signal line 30.

Figure 7:
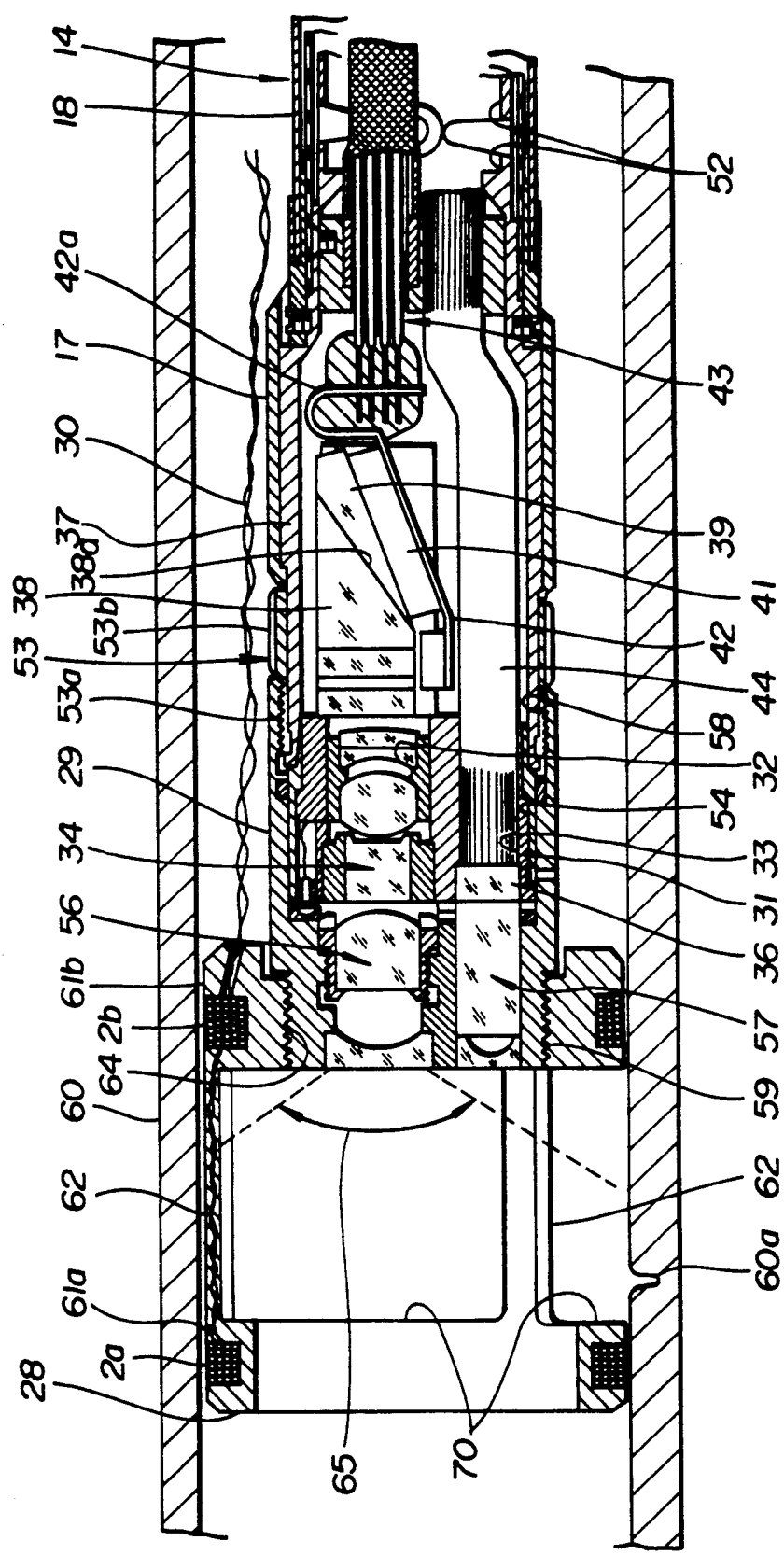

As shown in FIG. 7, the above mentioned tip part 17 of the above mentioned endoscope 7 is provided with a rigid substantially columnar tip forming member 31 provided with an observing through hole 32 and illuminating through hole 33. The above mentioned observing through hole 32 is provided with an objective lens system 34. The above mentioned illuminating through hole 33 is provided with an illuminating light transmitting lens system 36. A cylindrical member 37 is fixed as fitted from outside in the rear part of the above mentioned tip forming member 31. Within the above mentioned cylindrical member 37, a first prism 38 is provided on the optical axis of the above mentioned objective lens system 34 with a slope 38a directed rearward and further a second prism 39 formed like a wedge is provided on this slope 38a with the acute angle part directed forward. A solid state imaging device 41 is provided on the rear end surface of the above mentioned second prism 39. An object image is to be formed on the imaging surface of the above mentioned solid state imaging device 41 by the objective lens system 34 and converted to an electric signal. The above mentioned solid state imaging device 41 is provided on a substrate 42 fitted with an electronic circuit or the like. A signal line connecting part 42a is formed at the rear end of the above mentioned substrate 42 and a plurality of signal lines 43 are connected to the above mentioned signal line connecting part 42a. The above mentioned signal lines are to be connected to a video signal processing circuit (not illustrated) built-in in the above mentioned CCU 9 through the above mentioned insertable part 14, operating part 16, universal cord 22, light source connector 23, signal universal cord 24 and signal connector 26.

A light guide fiber bundle 44 having an exit end surface on the rear end surface of the above mentioned illuminating light transmitting lens system 36 and transmitting an illuminating light is inserted through the above mentioned cylindrical member 37 and is connected to the above mentioned light source apparatus 8 through the insertable part 14, operating part 16, universal cord 22 and light source cord 23.

Figure 8:
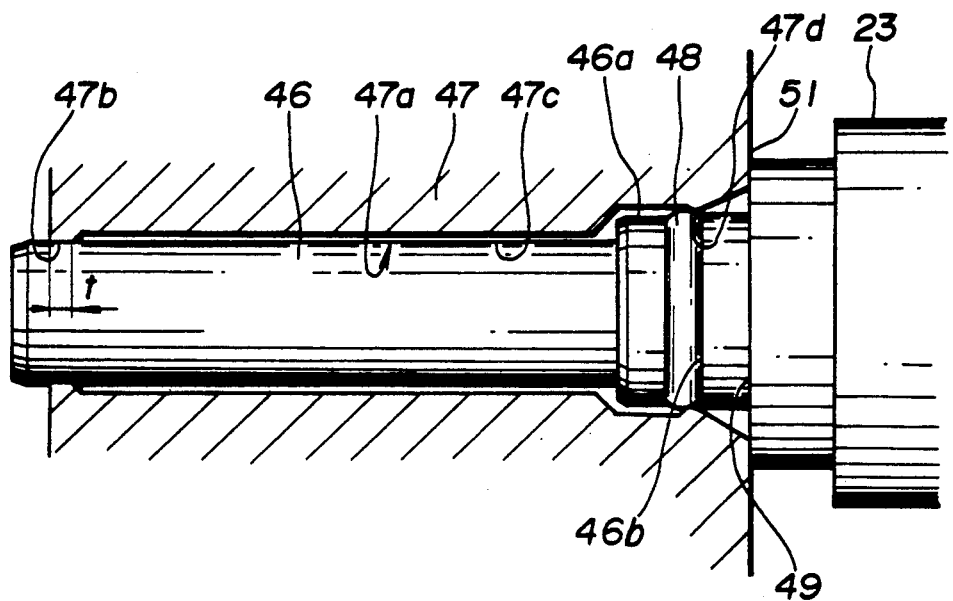
Figure 9:
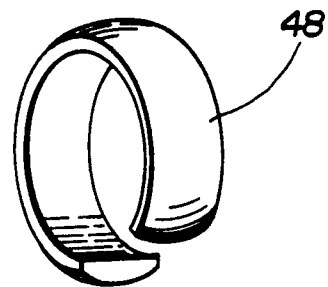

As shown in FIG. 8, the above mentioned light source connector 23 is provided with a cylindrical plug 46 which is to be inserted and connected into a socket 47 provided in the above mentioned light source apparatus 8. The above mentioned light guide fiber bundle 44 is inserted through the above mentioned plug 46 and the entrance end surface of the above mentioned light guide fiber bundle 44 is provided in the tip part of the above mentioned plug 46. An illuminating light emitted out of a lamp (not illustrated) provided within the above mentioned light source apparatus 8 is to be condensed and radiated on the entrance end surface of the above mentioned light guide fiber bundle 44.

The above mentioned plug 46 is formed on the base end side of a large diameter part 46a larger in diameter than the tip part so as to be stronger on the base end side. The above mentioned large diameter part 46a is peripherally provided with a groove 46b in which is fitted a C-ring 48 shown in FIG. 9. When the above mentioned large diameter part 46a is provided with the above mentioned C-ring 48, the C-ring diameter will be able to be also made larger and the removably fitting force of the above mentioned plug 46 will be able to be stabilized. An inserting through hole 47a through which the above mentioned plug 46 is to be inserted is formed in the above mentioned socket 47. A supporting part 47b of an inside diameter somewhat larger than the outside diameter of the tip part of the above mentioned plug 46 is formed on the tip side of the above mentioned inserting through hole 47a. An intermediate diameter part 47c of an inside diameter larger than the inside diameter of the above mentioned supporting part 47b is formed on the base end side of the above mentioned supporting part 47b. A projection 47d is formed peripherally in a position on the base end side of the above mentioned intermediate diameter part 47c and corresponding to the above mentioned large diameter part 46a. The length t in the axial direction of the above mentioned supporting part 47b is, for example, 1 mm. When the plug 46 is supported on the side nearest to the tip, the backlash in the diametral direction of the end surface of the plug tip part will be able to be controlled as much as possible and the condensed illuminating light from the lamp will be able to be led to the above mentioned light guide fiber bundle 44 without being wasted.

The inside diameter of the above mentioned projection 47d is to always press the slope of the above mentioned C-ring 48 and to energize the plug root end surface 49 in the direction of being always pressed against the socket end surface 51 so as to eliminate the backlash in the axial direction of the plug tip part. The above mentioned plug 46 is provided in such a position that, in case the above mentioned plug 46 is to be connected to the above mentioned socket 47, when the left side slope of the above mentioned C-ring 48 in FIG. 8 contacts the above mentioned projection 47d, the tip part of the above mentioned plug 46 will have been inserted through the above mentioned supporting part 47b so that, when the above mentioned C-ring 48 has passed over the above mentioned projection 47d, the tip part of the above mentioned plug 46 will be prevented from staggering and the above mentioned plug 46 will be prevented from being twisted. Further, when the above mentioned projection 47d is made small, a clicking sense may be obtained.

Returning to FIG. 7, among a plurality of bending frames 52 forming the above mentioned bendable part 18, the bending frame 52 at the foremost end is connected to the above mentioned cylindrical member 37 at the rear end. A connecting ring 53 is rotatably fitted from outside on the outer peripheral surface of the middle part of the above mentioned cylindrical member 37. A male screw part 53a is formed on the tip side on the outer peripheral surface of the above mentioned connecting ring 53 and a finger hanging part 53b for rotating the above mentioned connecting ring 53 is formed on the rear part of the connecting ring 53.

The above mentioned optical adapter 29 is fitted to the above mentioned tip forming member 31, is substantially columnar and is provided at the rear end with a recess 54 in which the above mentioned tip forming member 31 is inserted. A female screw part 58 to be screwed with the above mentioned male screw part 53a is provided on the inner peripheral surface of the rear end part of the above mentioned recess 54. A visual field angle exchanging lens system 56 is provided as aligned in the optical axis with the above mentioned objective lens system 34 when fitted to the tip forming member 31 and a light distributing lens system 57 is provided as aligned in the optical axis with the illuminating light transmitting lens system 36.

A male screw part 59 is formed on the outer peripheral surface of the tip part of the above mentioned optical adapter 29 so that the above mentioned eddy current flaw detecting probe 28 may be screwed onto the above mentioned male screw part 59.

The above mentioned eddy current flaw detecting probe 28 is formed to be substantially cylindrical by connecting two ring-like members 61a and 61b of an outside diameter somewhat smaller than the inside diameter of the above mentioned pipe 60 to be inspected with each other through a plurality of stays 62. The above mentioned coil 2a shown in FIG. 3 is wound on the above mentioned ring-like member 61a on the tip side and the above mentioned coil 2b shown in FIG. 3 is wound on the above mentioned ring-like member 61b on the rear end side. The above mentioned ring-like members 61a and 61b and the above mentioned stays 62 form observing windows 70 which are in the visual field range 65 of the above mentioned visual field angle exchanging lens system 56 so that the above mentioned flaw 60a produced on the wall surface of the above mentioned pipe 60 may be observed with a naked eye or the like from the above mentioned observing windows 70.

The above mentioned coils 2a and 2b are connected with each other by signal lines arranged within the above mentioned stays 62 and further the above mentioned coil 2b is connected to the above mentioned signal lines 30 arranged along the outer periphery of the above mentioned insertable part 14. A female screw part 64 is formed on the inner peripheral surface of the above mentioned ring-like member 61b on the rear end side and is screwed with a male screw part 59 provided on the above mentioned optical adapter 29 to connect the above mentioned optical adapter 29 and eddy current flaw detecting probe 28 with each other.

The above mentioned eddy current flaw detecting apparatus is formed as shown in FIG. 10.

The above mentioned coils 2a and 2b provided in the above mentioned eddy current flaw detecting probe 28 are connected to the above mentioned bridge circuit 1 shown in FIG. 2. The above mentioned bridge circuit 1 is connected to the above mentioned oscillator 3 as a power source, an automatic balancer 68 and an amplifier 66. In case the above mentioned coil 2 corresponding to the inside diameter of the above mentioned pipe 60 to be inspected is connected to the above mentioned bridge circuit 1, the above mentioned automatic balancer 68 will automatically keep the balance of impedances as explained in FIG. 2. The above mentioned amplifier 66 is to amplify the amplitude of the output signal obtained as a result of the inspection. A synchronous detector 67 is connected to the above mentioned amplifier 66 and a phase shifter 69, compares the phase of the output of the above mentioned amplifier 66 and the phase of the output of the above mentioned phase shifter 69 with each other and outputs as a flaw sensing signal, for example, the direct current voltage proportional to the difference of the phase produced by the above mentioned flaw 60a. The above mentioned phase shifter 69 can freely adjust the phase of the output of the above mentioned oscillator 3. The output of the above mentioned synchronous detector 67 is connected to the above mentioned automatic balancer 68, a CRT display 71 and a trigger circuit 72 as a timing signal generating means. The above mentioned CRT display 71 is to display as an image the direct current voltage from the above mentioned synchronous detecting circuit 67. The above mentioned trigger circuit 72 is connected to the above mentioned VTR 11, outputs to the above mentioned VTR 11 an on/off signal controlling a recording operation and non-operation by receiving the direct current voltage from the above mentioned synchronous detecting circuit 67 and controls the operation of the above mentioned VTR 11.

The operation of the thus formed endoscope apparatus shall be explained.

The illuminating light fed from the above mentioned light source apparatus 8 will be transmitted through the above mentioned light guide fiber bundle 44, will be emitted out of the above mentioned light distributing lens system 57 through the above mentioned illuminating light transmitting lens system 36 and light distributing lens system 57 and will be radiated onto the inner peripheral surface of the above mentioned pipe 60 through the above mentioned observing window 70. The reflected light from the inner peripheral surface of the above mentioned pipe 60 will pass through the above mentioned observing window 70 and will form an image on the imaging surface of the above mentioned solid state imaging device 41 through the above mentioned visual field angle converting lens system 56 and objective lens system 34. The formed optical image will be converted to an electric signal by the above mentioned solid state imaging device 41 and the electric signal will be output to a video signal processing circuit (not illustrated) of the above mentioned CCU through the above mentioned signal lines 43. A video signal will be produced from the input electric signal in the video signal processing circuit and will be output to the above mentioned VTR 11 and monitor 12 and the image of the inner peripheral surface of the above mentioned pipe 60 will be displayed on the picture in the above mentioned monitor.

The eddy current flaw detecting probe 28 is advanced in the direction indicated by the arrow in FIG. 11. When the above mentioned coil 2a on the tip side reaches the flaw 60a as shown in FIG. 11(C), an output voltage will be obtained from the bridge circuit 1. This output voltage will be amplified in the amplifier 66 and will be output to the synchronous detector 67. In case the signal voltage to be measured from the amplifier 66 is $e = E \cos(\omega t + \Phi)$ against the reference voltage $e_0 = E_0 \cos \omega t$ input from the phase shifter 69, such a direct current output voltage as is proportional to $E \cos \Phi$ will be obtained in the synchronous detector 67. The direct current output voltage will be output to the CRT display 71 and trigger circuit 72. As shown in FIGS. 11(A) and (B), positive and negative trigger levels are set in the above mentioned trigger circuit 72. When a signal S1 of a voltage level higher than this trigger level is input, the control signal of the recording operation will be on for the VTR 11 which will receive the on-signal and will begin to record the video signal of the endoscope image input from the CCU.

Figure 11A:
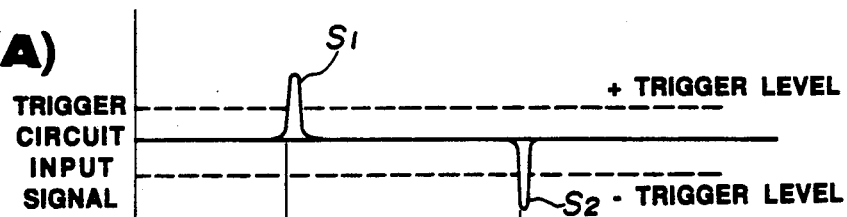
FIGS. 11(A) to (B) are explanatory views of timings of on/off signals operating a video tape recorder.
Figure 11B:
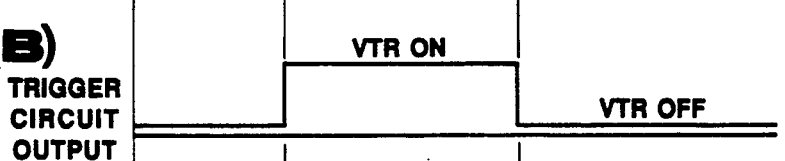
Figure 11C:
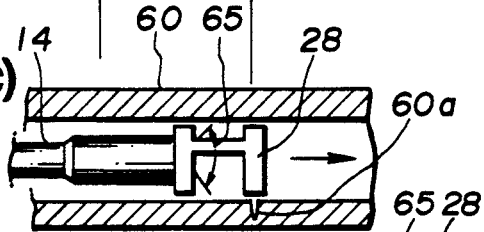
Figure 11D:
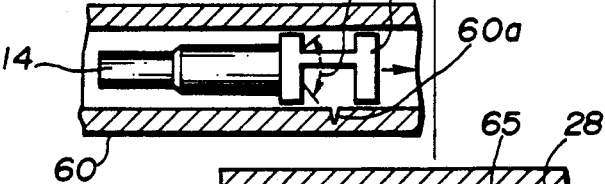
Figure 11E:
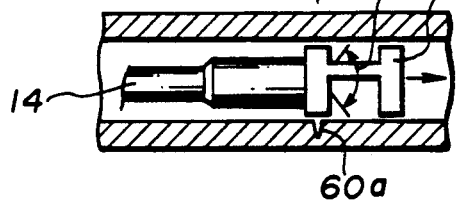

As shown in FIG. 11(D), when the above mentioned eddy current flaw detecting probe 28 is advanced in the direction indicated by the arrow, the flaw 60a will be able to be seen from the observing window 70 and will be recorded in the above mentioned VTR. When the eddy current flaw detecting probe 28 is further advanced, as shown in FIG. 11(E), the flaw 60a will come out of the visual field range 65. When the coil 2b on the rear end side reaches the flaw 60, a signal S2 of a polarity opposite to that of the signal S1 will be output to the trigger circuit 72 from the synchronous detector 67 in the same manner as is described above. The trigger circuit 72 will receive it and will switch off the control signal of the recording operation and the VTR will stop the recording.

As described above, in this embodiment, depending on whether the flaw 69a is present or not, the recording operation of the VTR 11 can be controlled to be on/off and therefore a useless recording can be prevented.

When the insertable part 14 fitted with the eddy current flaw detecting probe 28 is inserted into the pipe 60 by a motor or the like, the inspection will be able to be perfectly automated and, after the end of the inspection, the inspector will be able to confirm the result of the eddy current flaw detection and the image recorded in the above mentioned VTR 11.

The signal from the eddy current flaw detecting apparatus 13 may be synthesized with a video signal and may be recorded in the VTR.

Character data may be superimposed on the VTR by the trigger signal.

The eddy current flaw detecting probe 28 plays a centering role of positioning the endoscope 7 in the axial center of the pipe 60.

In this embodiment, a moving picture is recorded in the VTR but, after the on-signal from the trigger circuit 72 is received, when the flaw 69a is positioned in the observing window 70 and enters the above mentioned visual field range 65, a release signal may be output for photographing.

In this embodiment, the eddy current flaw detecting probe 28 is fitted to the optical adapter 29 but may be fitted directly to the tip part 17 of the endoscope 7.

In FIG. 12 is shown the second embodiment of the present invention.

In this embodiment, the eddy current flaw detecting probe 28 and optical adapter 29 explained in FIGS. 1 and 7 of the first embodiment are made integral with each other. The same component members as in the first embodiment shall bear the same reference numerals and shall not be explained here.

An eddy current flaw detecting probe 28 in this embodiment is formed, for example, of a resin or the like having an electric insulation, is fitted at the rear end with an optical adapter 29 at the tip from outside and is fixed with a bonding agent or the like.

An electric contact 76 is provided on the tip surface of the tip part 17 and is to be electrically connected with an electric contact 77 provided in the optical adapter 29 in case the optical adapter 29 is fitted to the above mentioned tip part 17. A signal line 78 inserted through the insertable part 14 is connected to the electric contact 76 on the tip part 17 side and is connected to the eddy current flaw detecting apparatus 13 through the insertable part 14, operating part 16 and universal cord 22. The electric contact 77 on the optical adapter 29 side is formed, for example, of a conductive rubber so as to improve the mechanical contact with the electric contact 76 of the tip part 17 and is connected with the coil 2b on the rear end side through a signal line 79 arranged within the optical adapter 29.

The other formations and operations are the same as in the first embodiment.

According to this embodiment, the optical adapter 29 and eddy current flaw detecting probe 28 are made integral with each other and therefore can be simply removably fitted to the endoscope 7.

Also, as the eddy current flaw detecting electric contact 76 is provided in the endoscope 7, the wiring from the coil 2 will not be exposed out of the endoscope 7 and accidents such as a line break and current leak will be able to be prevented.

The other effects are the same as in the first embodiment.

In FIG. 13 is shown the third embodiment of the present invention.

In the first and second embodiments, the eddy current flaw detecting probe 28 is removably fitted to the endoscope 7, whereas, in this embodiment, the eddy current flaw detecting coil 2 is provided just after the bendable part 18 of the insertable part 14 (on the operating part 16 side). The same component members as in the first embodiment shall bear the same reference numerals and shall not be explained here.

As shown in FIG. 13, the insertable part 14 is provided with the tip part 17, bendable part 18 and flexible tube part 19 as connected in the order mentioned from the tip side. The eddy current flaw detecting coil 2 is provided just after the above mentioned bendable part 18 within the above mentioned flexible tube 19 so as to surround the periphery of signal lines 43 connected to a solid state imaging device 41 and light guide fiber bundle 44 and is connected to the eddy current flaw detecting apparatus as explained in FIGS. 1 and 10.

The other formations are the same as in the first embodiment.

In this embodiment, when inspecting the flaw 60a, first the insertable part 14 is inserted deep into the pipe 60 and is then inspected while being pulled out. The inspecting method shall be explained in the following.

When the insertable part 14 is pulled out and the coil 2 passes the part in which the flaw 60a is generated in the pipe 60, as explained in FIGS. 1, 10 and 11 of the first embodiment, the operation controlling signal of the VTR 11 will be on from the trigger circuit 72 of the eddy current flaw detecting apparatus 13. The VTR 11 will receive the on-signal and will begin to record the endoscope image. When a preset time has elapsed and the flaw 60a comes out of the visual field range 65 of the objective lens system 34 (the visual field angle converting lens system 56 when the optical adapter 29 is fitted), the recording will be stopped. The other operations are the same as in the first embodiment.

In this embodiment, the eddy current flaw detecting coil 2 is provided in the front part of the flexible tube part 19 just after the bendable part 18 but, as the signal lines 43 of the solid state imaging device 41 and the light guide fiber bundle 44 are only inserted through the flexible tube part 19, there will be a utilizable space larger than on the tip side from the bendable part 18. Therefore, when the coil 2 is provided in this part, the insertable part will be able to be prevented from becoming large in diameter.

The other effects are the same as in the first embodiment.

Figure 14:
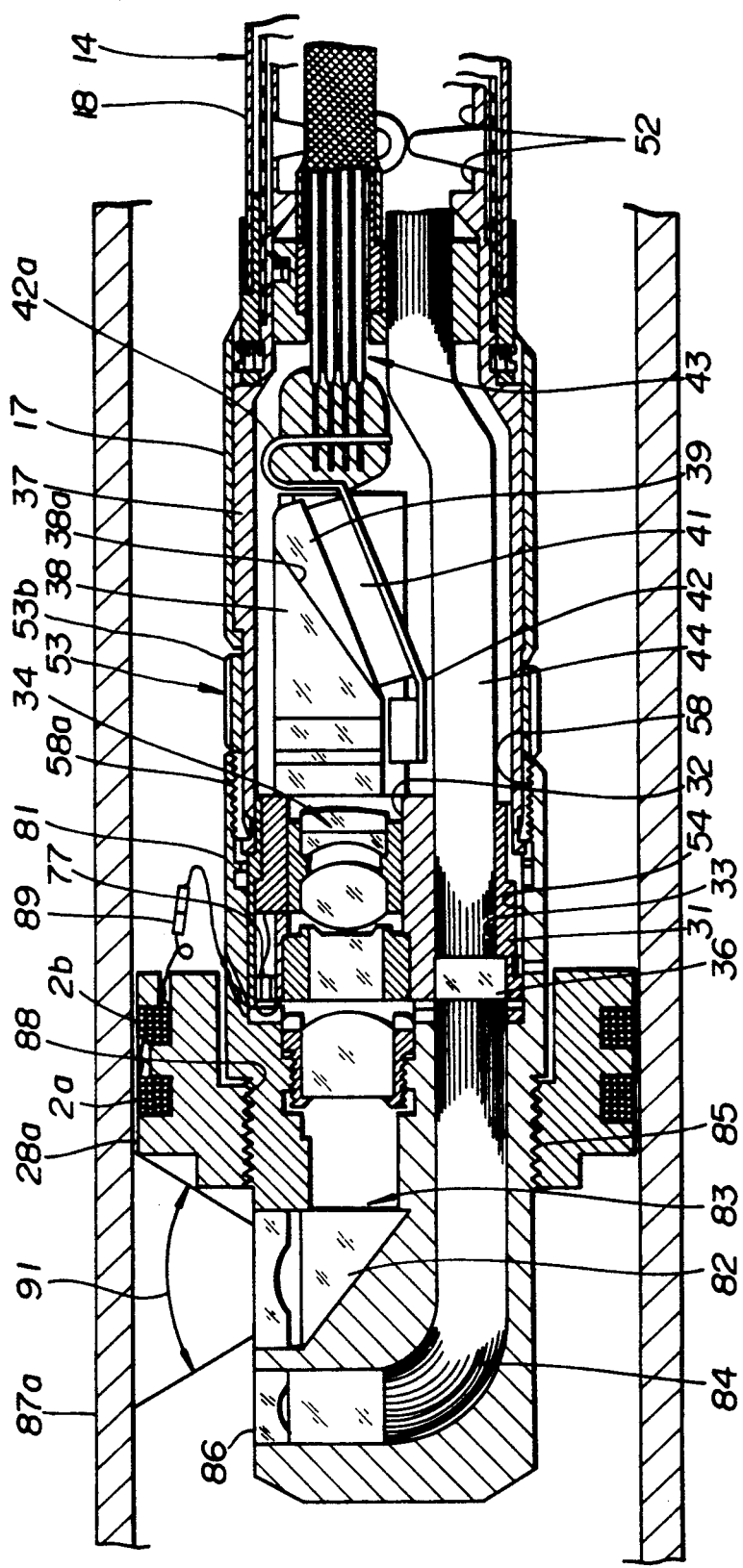
FIGS. 14 and 15 relate to the fourth embodiment of the present invention.
Figure 15:
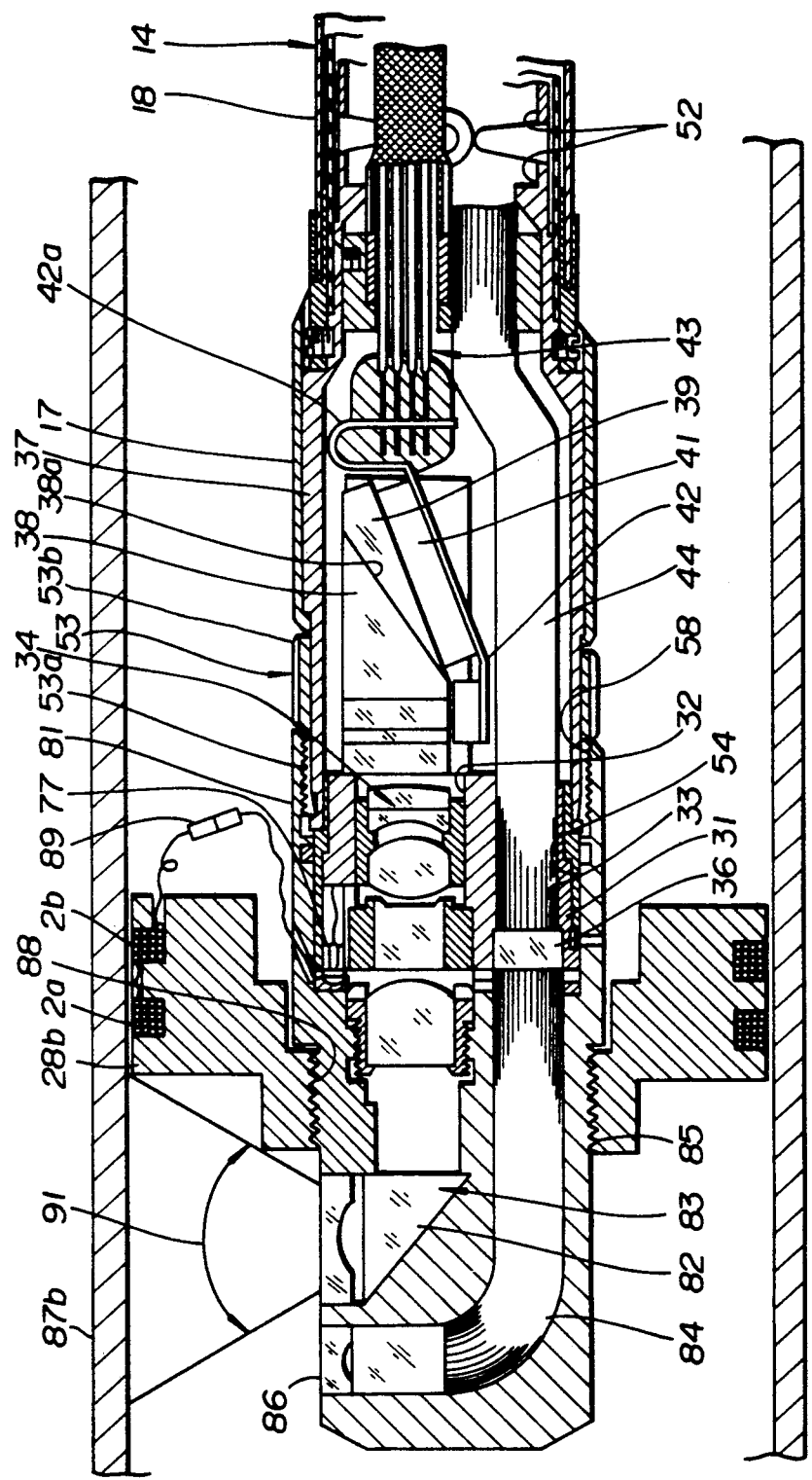

In FIGS. 14 and 15 is shown the fourth embodiment of the present invention.

The optical adapter of this embodiment is a side viewing adapter. The same component members as in the first embodiment shall bear the same reference numerals and shall not be explained here.

An optical adapter 81 for side viewing is removably provided in the tip part 17 of the insertable part 14 of this embodiment and is provided with a visual field direction converting lens system 83 including a prism 82 so as to be aligned in the optical axis with the objective lens system. The prism 82 has the optical axis in the axial direction of the insertable part 14 made bendable in the peripheral direction intersecting at right angles with the axial direction so as to obtain a visual field in the diametral direction. Within the optical adapter 81 is provided a light guide fiber bundle 84 in which the entrance end surface coincides with the illuminating light transmitting lens system 36 of the tip part 17 and the exit end surface illuminates the visual field direction of the visual field direction converting lens system 83. On the exit end surface of the light guide fiber bundle 84, a light distributing lens system 86 is provided.

A male screw part 85 is formed in the rear of the visual field direction converting lens system 83 on the outer peripheral surface of the optical adapter 81. The eddy current flaw detecting probe 28a or 28b is removably screwed onto the male screw part 85. The eddy current flaw detecting probe 28a is to be used for a fine diameter pipe 87a as shown in FIG. 14 and the eddy current flaw detecting probe 28b is to be used for a pipe 87b of a diameter larger than of the pipe 87a as shown in FIG. 15.

The eddy current flaw detecting probes 28a and 28b are ring-like. On the inside surface of each of them is formed a female screw part 88 to be screwed with the male screw part 85. The outside diameter of the eddy current flaw detecting probe 28a is somewhat smaller than the inside diameter of the pipe 87a of a fine diameter and the outside diameter of the eddy current flaw detecting probe 28b is somewhat smaller than the inside diameter of the pipe 87b of a large diameter. On the outer peripheral surface, on the tip side is provided an eddy current flaw detecting coil 2a and on the rear end side is provided an eddy current flaw detecting coil 2b. The coils 2a and 2b are electrically connected with each other. The coil 2b is connected with an electric contact 77 provided in the optical adapter 81 by a small connector 89. As explained in FIG. 1 of the first embodiment, in case the optical adapter 81 is fitted to the tip part 7, the electric contact 77 will be connected with an electric contact 76 of the tip part 17.

When fitted to the optical adapter 81, the eddy current flaw detecting probes 28a and 28b will not enter the visual field range 91 of the visual field direction converting lens system 83 and the coil 2 will be positioned near the visual field range 91.

The other formations are the same as in the first embodiment.

In this embodiment, in case the pipe 87a of a fine diameter is to be inspected, the eddy current flaw detecting probe 28a is fitted to the optical adapter 81 and, in case the pipe 87b of a diameter larger than of the pipe 87a is to be inspected, the eddy current flaw detecting probe 28b is fitted to the optical adapter 81.

The inspection is carried out while pulling the insertable part 14 out of the pipe 87a or 87b. When the coil 27a or 27b passes the part in which the flaw 60a of the inside wall of the pipe 87a or 87b is generated, as explained in FIGS. 10 and 11 of the first embodiment, an on-signal for starting a recording operation will be output to the VTR 11 from the trigger circuit 72 forming the eddy current flaw detecting apparatus 13 and the recording of the inside wall image of the pipe 87a or 87b will be started. As the coil 2 is provided adjacently to the visual field range 91 of the visual field direction converting lens system 83, as soon as the recording is started, the flaw 60a will be displayed within the image.

When the flaw 60a is detected with the eddy current flaw detecting apparatus 13 and is precisely observed with the side viewed image of the endoscope 7, the coil 2 had better be located near the visual field. However, as the coil 2 is made in conformity with the inside diameter of the pipe 87a or 87b, if the position relation between the visual field direction converting lens system 83 and the coil 2 is the same, for the eddy current flaw detecting probe 28b with a large inside diameter, a part of the visual field range 91 will be obstructed by the contour of the eddy current flaw detecting probe 28b and a part of the image will be missing in some cases.

In this embodiment, as the position of the coil 2 is varied in response to the diameter of the coil 2, the visual field range 91 of the endoscope 7 will not be obstructed, as the coil 2 is provided outside the visual field range 91, a part of the image will not be missing and, as the coil 2 is arranged near the visual field range 91, the detection of the flaw 60a by the coil 2 and the endoscope observation will be able to be smoothly made.

The other operations and effects are the same as in the first embodiment.

In this embodiment, the side viewing optical adapter 81 has been explained but the invention may be applied to the straight viewing optical adapter 29 explained in FIG. 7 of the first embodiment.

In FIGS. 16 to 21 is shown the fifth embodiment of the present invention.

This embodiment has an automatic inserting apparatus to control the inserting speed of the insertable part by detecting whether a flaw is present or not with the eddy current flaw detecting apparatus. The same component members as in the first embodiment shall bear the same reference numerals and shall not explained here.

Figure 16:
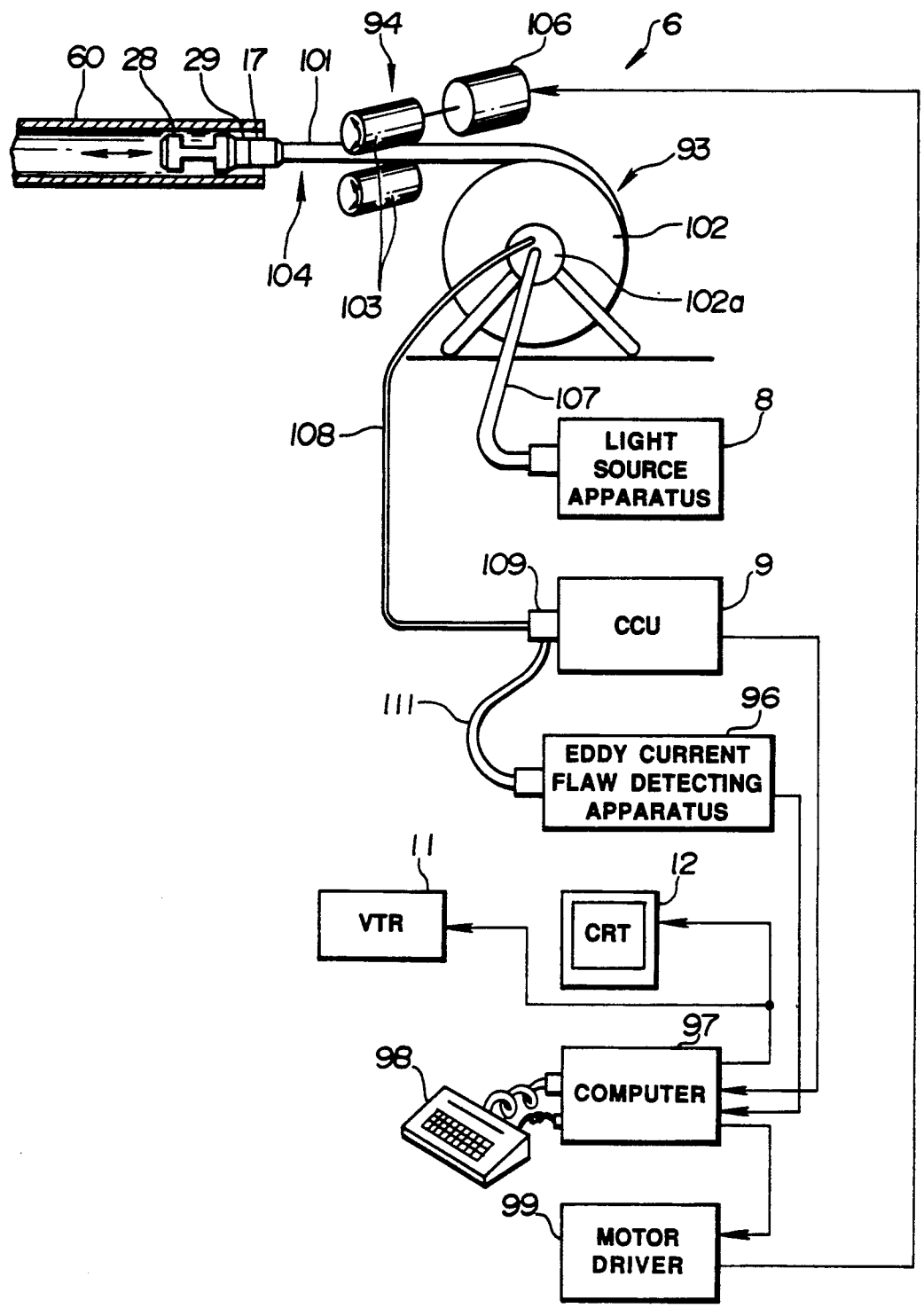

As shown in FIG. 16, an endoscope apparatus 6 of this embodiment comprises a drum type endoscope 93, automatic inserting apparatus 94, light source apparatus 8, CCU 9, eddy current flaw detecting apparatus 96, monitor 12, VTR 11, computer 97, keyboard 98 and motor driver 99.

The above mentioned drum type endoscope 93 has the tip part 17 explained in FIGS. 1 and 7 and a long flexible part 101 is connected to the tip part 17 at the rear end. The tip part 17 and flexible part 101 form an insertable part 104 The optical adapter 29 explained in FIGS. 1 and 7 of the firs:& embodiment is removably fitted to the tip part 17. The eddy current flaw detecting probe 28 explained in FIGS. 1 and 7 of the first embodiment is removably provided in the optical adapter 29.

The flexible part 101 is connected at the base end to a drum 102 on which the flexible part 101 is to be wound up. Also, the flexible part 101 is supported by rollers 103 so as to be freely inserted through or pulled out of the pipe 60 when the rollers 103 are rotated and driven by the motor 106.

A light guide cable 107 for feeding an illuminating light to the drum type endoscope 93 and a signal cable 108 for transmitting an image signal output from the drum type endoscope 98 are extended out of one bearing part of the drum 102. The light guide cable 107 is connected to the light source apparatus 8. The signal cable 108 is connected to the CCU. A signal cable 111 is extended out of a connector 109 of the signal cable 108 and is connected to the eddy current flaw detecting apparatus 96.

The CCU and eddy current flaw detecting apparatus 96 are connected to the computer 97 which can input a video signal from the CCU 9 and a flaw detecting signal as a flaw sensing signal from the eddy current flaw detecting apparatus 96. The computer 97 is connected to the monitor 12, VTR 11 and motor driver 99 so as to output an analyzing signal to the monitor 12 and VTR 11 and a motor controlling signal to the motor driver 99.

The keyboard 98 is connected to the computer 97 so that data and control signals may be input from the keyboard 98.

Figure 17:
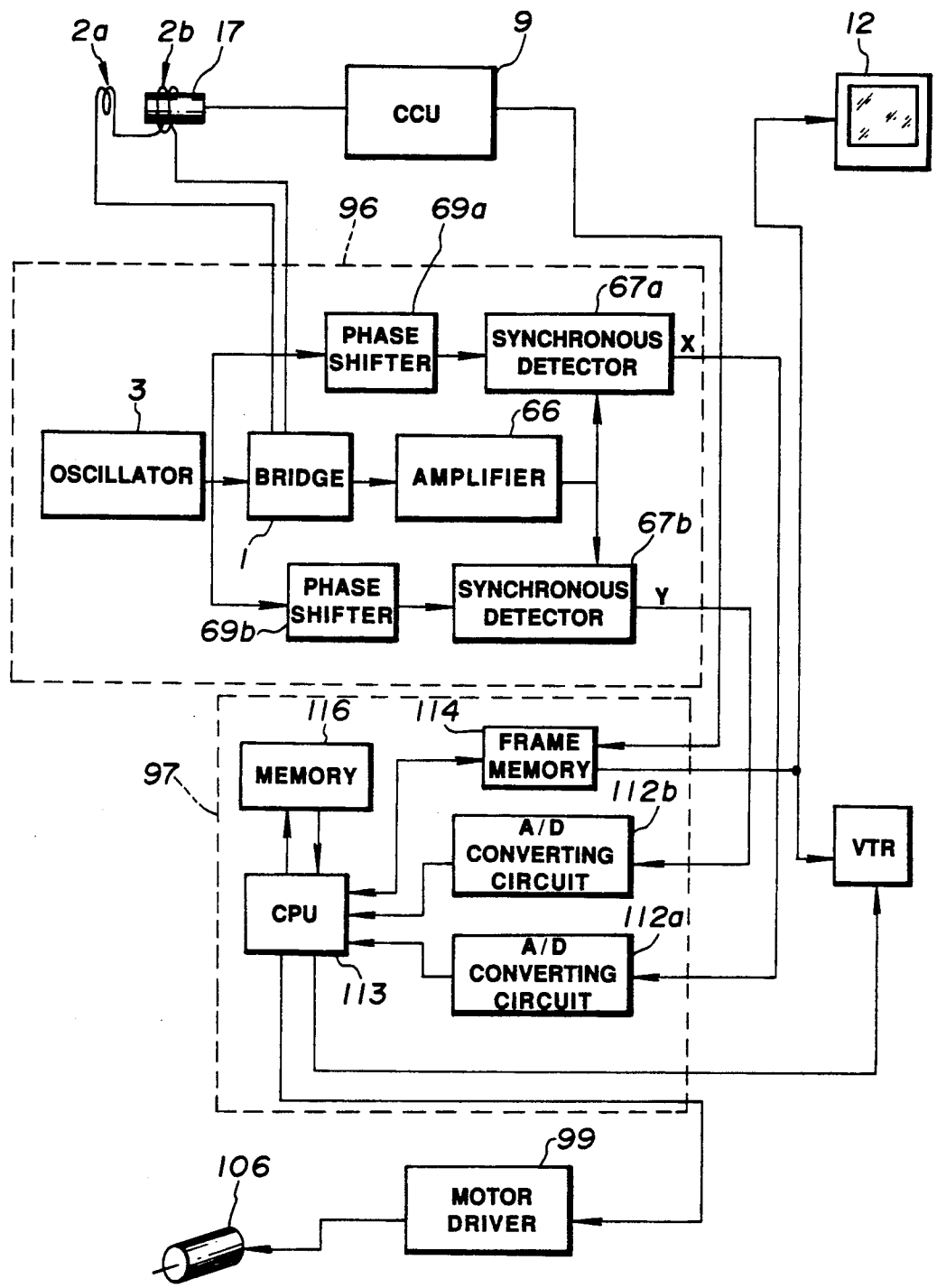

The eddy current flaw detecting apparatus 96 and computer 97 are formed as in FIG. 17.

The eddy current flaw detecting apparatus 96 is fundamentally the same as the eddy current flaw detecting apparatus 13 explained in FIG. 10 of the first embodiment but is different in respect that respectively two of the phase shifter 69 and synchronous detector 67 are provided. The phase shifter 69a and synchronous detector 67a are to analyze the phase in the X axis direction and the phase shifter 69b and synchronous detector 67b are to analyze the phase in the Y axis direction. The synchronous detectors 67a and 67b are connected respectively to A/D converters 112a and 112b of the computer 97 so that the output X of the synchronous detector 67a may be digitalized by the A/D converter 112a and the output Y of the synchronous detector 67b may be digitalized by the A/D converter 112b. The A/D converters 112a and 112b are connected to a CPU 113 so that various analyses may be made in the CPU 113.

FIG. 18 represents in an XY plane the outputs X and Y of the two synchronous detectors 67a and 67b. FIG. 18(A) shows a vector pattern when there is an inside surface flaw. FIG. 18(B) shows a vector pattern when there is an outside surface flaw. FIG. 18(C) shows a vector pattern where there is a noise by the vibration of the eddy current detecting probe 28.

A frame memory 114, memory 116 and the motor driver 99 are connected to the CPU 113. The frame memory 114 is connected to the CCU so that a video signal may be taken input, processed and output to the monitor 12. The memory 116 is to house the programs and data for the operation by the CPU 113. The motor driver 99 is to control the motor 106 inserting and pulling out the insertable part 104 so that the insertable part 104 may be rotated and driven, stopped, inserted and pulled out at a high speed and inserted and pulled out at a low speed.

The other formations are the same as in the first embodiment.

In the thus formed embodiment, when an inspection is to be made, a control signal for starting the inspection is input into the CPU 113 of the computer 97 from the keyboard 98. The CPU 113 will instruct a high speed rotation to the motor driver 99 and the motor driver 99 will rotate and drive the motor 106 at a high speed so that the rollers 103 will rotate and the insertable part 104 will be inserted at a high speed into the pipe 60. When a flaw 60a is generated on the inside surface of the pipe 60, as the tip side coil 2a passes the part in which the flaw 60a is present, the signal shown in the region A shown in FIG. 19 will be input into the CPU 113. In case the signal appears in the region A, the CPU 113 will output a signal A' shown in FIG. 20(A) to the motor driver 99. The motor driver 99 will output a control signal to the motor 106 so as to receive the signal A' and switch the rotation speed from high speed to a low speed so that the motor 106 will reduce the inserting speed of the insertable part 104 to a low speed. Also, the CPU 113 will instruct the frame memory 114 to enhance the outline of the flaw 60a and will superimpose on the endoscope image the vector pattern shown in FIG. 18(A) The video signal thus processed in the image and having had the vector pattern superimposed will be output to the monitor 12 and VTR 11. The image shown in FIG. 21 will be displayed on the monitor 12 and the video signal will be recorded in the VTR. In FIG. 21, the reference numeral 118 represents the flaw 60a and 119 represents a vector pattern.

When the insertable part 104 is inserted and the coil 2b passes the part in which the flaw 60a is present, the signal in the region B shown in FIG. 19 will be input into the CPU 113. In case the signal appears in the above mentioned region B, the CPU 113 will output the signal B' shown in FIG. 20(A) to the motor driver 99. When the signal B' is received, the motor driver 99 will switch the control signal to the motor 106 to rotate at a high speed so that the inserting speed of the insertable part 104 will be a high speed. The CPU 113 will stop the recording of the VTR.

The other operations are the same as in the first embodiment.

In this embodiment, as the inserting speed of the insertable part 104 is controlled by the presence or absence of the flaw 60a, only the flaw 60a can be precisely observed.

In the part wherein the flaw 60a is not present, as the insertable part 104 is inserted at a high speed, the inspecting time can be reduced and the inspecting efficiency can be elevated.

The other effects are the same as in the first embodiment.

Figure 22:
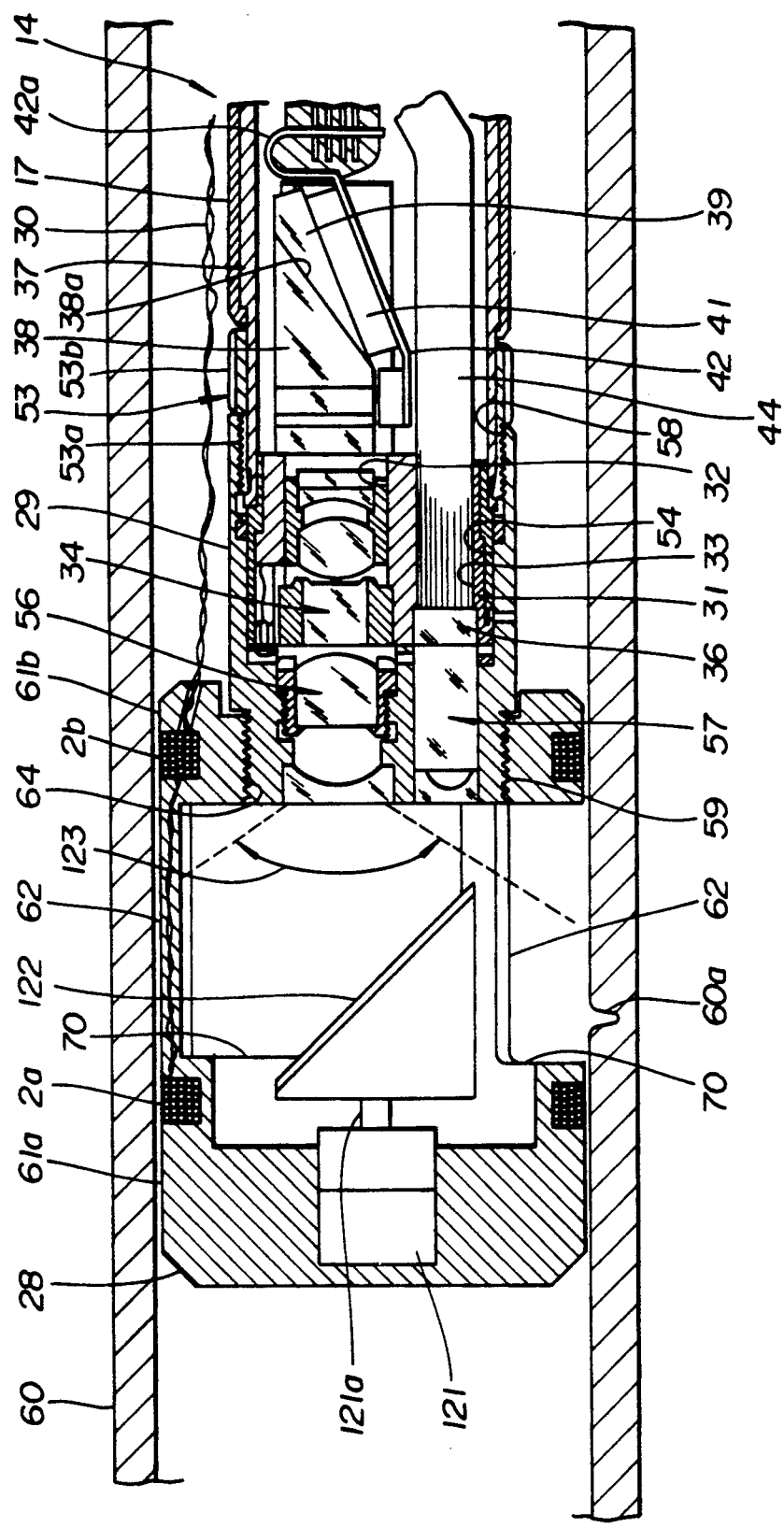
FIG. 22 is a sectioned view of an eddy current flaw detecting probe relating to the sixth embodiment of the present invention.

In FIG. 22 is shown the sixth embodiment of the present invention.

In this embodiment, a rotary mirror is provided to make an observation within the eddy current flaw detecting probe explained in FIGS. 1 and 7 in the first embodiment. The same component members as in the first embodiment shall bear the same reference numerals and shall not be explained here.

The ring-like member 61a on the tip side forming the eddy current flaw detecting probe 28 of this embodiment is provided with a motor 121 having a reduction gear built-in with a driving shaft 121a directed to the visual field angle converting lens system 56. Further, the driving shaft 121a is provided with a rotary mirror 122 to bend the optical axis of the visual field angle converting lens system 56 so that the inside wall image of the pipe 60 from the observing window 70 may be reflected to enter the visual field angle converting lens system 56. The rotary mirror 122 is rotated by the motor 121 so that the image of the entire periphery of the inside wall of the pipe 60 may enter the visual field angle converting lens system 56.

In this embodiment, as the rotary mirror 122 is provided, the visual field range 65 of the visual field angle converting lens system 56 can be made narrower than that of the visual field angle converting lens system explained in FIG. 7 of the first embodiment. Therefore, the distortion of the image displayed in the monitor 12 can be made small and a favorable image can be obtained.

The other operations and effects are the same as in the first embodiment.

In the first to sixth embodiments, the recording operation and inserting operation of the VTR 11 are controlled by detecting the flaw 60a but the other operations may be controlled.

In FIGS. 23 to 26 is shown the seventh embodiment of the present invention.

Figure 24:
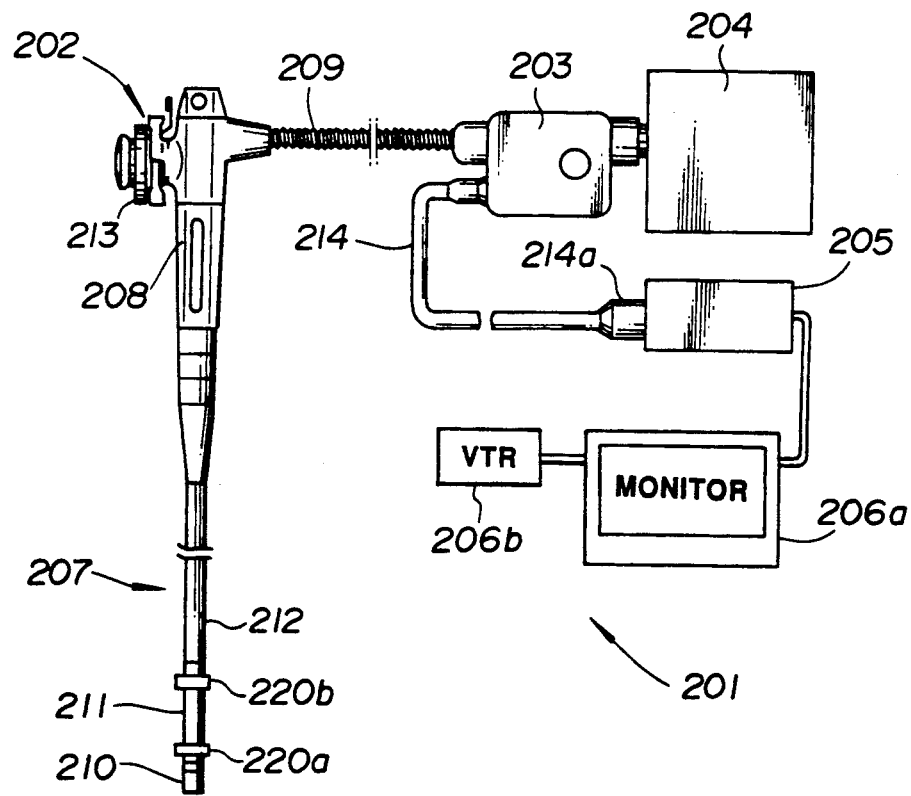

As shown in FIG. 24, an endoscope apparatus 201 comprises an endoscope 202 which is an electronic endoscope provided in the tip part with a solid state imaging device and flaw detection sensing member. A light source apparatus 204 feeds an illuminating light to the endoscope 202. A video processor 205 is provided with a video processing circuit driving the solid state imaging device of the endoscope 202 and converting the imaging signal from the solid state imaging device into a video signal. A flaw detecting signal processing circuit obtains the size or the like of a flaw or the like by a signal from a later described flaw detecting coil provided in the endoscope apparatus 201. A monitor 206a displays the video signal from the video processor 205. A VTR 206b records the video signal from the video processor 205.

The endoscope 202 comprises an insertable part 207 insertable into an object to be inspected, a thick operating part 208 provided as connected to the insertable part 207 on the hand base side and a universal cord 209 provided as extended out of the operating part 208 on the side.

The above mentioned universal cord 209 is provided at the end with a connector 209a which is to be removably connected to a connector apparatus 203.

The connector apparatus 203 is to be removably connected to the above mentioned light source apparatus 204 and is provided with a universal cord 214 extended from it.

The universal cord 214 is provided at the end with a connector 214a which is to be removably connected to the video processor 205.

The video processor 205 is connected to the monitor 206a and VTR 206b. The monitor 206a is to display the video signal from the video processor 205. The VTR 206b is to record the video signal from the video processor 205.

The insertable part 207 comprises a rigid tip part 210 internally provided with a solid state imaging device or the like, a bendable part 211 bendable, for example, vertically/horizontally and connected to the tip part 210 at the rear end and an elongate flexible tube part 212 connected to the bendable part 211 at the rear end.

The operating part 208 is provided with a bending operation knob 213 bending the bendable part 211 by hand. A bending wire (not illustrated) is connected at one end to the bending operation knob 213 and at the other end to the foremost one of a plurality of bending frames (not illustrated) forming the bendable part 211. When the bending operation knob 213 is, for example, rotated, the bending wire will be pulled to bend the bendable part 211.

In a position in the tip direction of the bendable part 211, a flaw detecting coil (mentioned as an EC coil hereinafter) 220a which is one of flaw detection sensing members and is to detect the position and size of a flaw or the like is provided on the outer periphery of the bendable part 211a and, in a position in the hand base side direction of the bendable part 211, the same EC coil 220b as the EC coil 220a is to be provided on the outer periphery of the bendable part 211.

Figure 23:
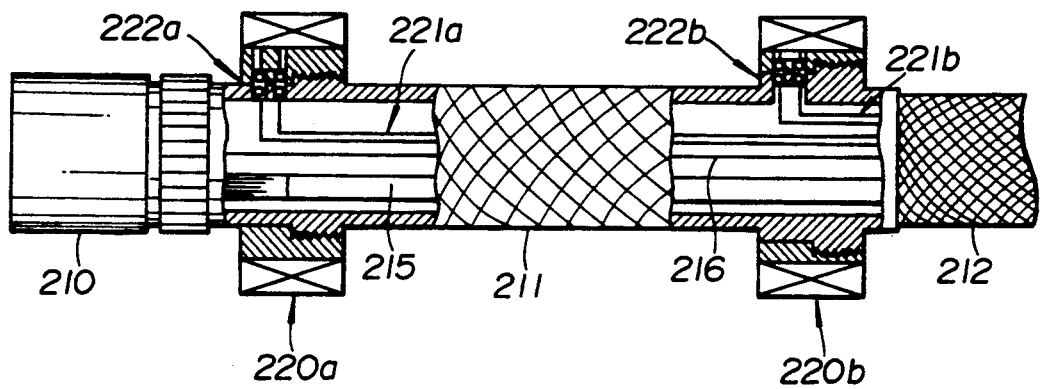

The details of the bendable part 211 and EC coils 220a and 220b shall be explained by using FIG. 23.

A plurality of bending frames (not illustrated) are connected and provided within the bendable part 211 so that, when the bending frames move in the bending direction respectively with the connecting parts as axes, the bendable part 211 will bend as described above.

Within the bendable part 211 are internally provided a light guide 215 leading an illuminating light from the light source apparatus to the tip part 210, a signal line 216 connected to the solid state imaging device, a signal line 221a connected to the EC coil 220a through a later described EC signal contact and a signal line 221b connected to the EC coil 220b through a later described EC signal contact. Screws are made on the outer periphery of the bendable part 211 on the tip side and rear end side so that the EC coils 220a and 220b may be respectively fitted. EC signal contacts 222a and 222b which are electric contacts are provided near the positions in which the screws are made. Of the screws made as described above, the outside diameter of the tip side screw is made smaller than the inside diameter of the EC coil 220b so as to make it easy to fit, for example, the EC coil 220b.

The above mentioned EC coils 220a and 220b are provided with the EC signal contacts 222a and 222b opposed respectively to the EC signal contacts 222a and 222b provided in the bendable part 211. The EC signal contacts 222a and 222b are connected to the coil 220 of the EC coils 220a and 220b.

One of the EC coils 220a and 220b may be a supporting member of the same contour formed, for example, of a synthetic resin instead of the EC coil 220a or 220b.

The operation of the thus formed endoscope apparatus shall be explained.

When the insertable part 207 is inserted into the pipe line 230 which is an object to be inspected, as shown, for example, in FIG. 25(A), the EC coils 220a and 220b will be in contact with a the EC coils 220a and 220b will not be stable and, in case the insertable part 207 is inserted or pulled, the position of the inner periphery of the pipe line 230 in which a flaw is to be detected by the EC coils 220a and 220b will not be in a fixed direction.

However, when the bending operation knob 213 is operated to bend the bendable part 211, as shown, for example, in FIG. 25(B), the tip part 210 and the inner periphery of the pipe line 230 will contact with each other and the EC coil 220b and the inner periphery of the pipe line 230 will contact with each other so that the position of the inner periphery of the pipe line 230 in which a flaw is to be detected by the EC coils 220a and 220b will be in a fixed direction. Also, depending on the bending angle, the EC coil 220a and the inner periphery of the pipe line 23 will contact with each other and the EC coil 220b and the inner periphery of the pipe line 230 will contact with each other so that, in the same manner, the position of the inner periphery of the pipe line 230 in which a flaw is to be detected by the EC coils 220a and 220b will be in a fixed direction.

When detecting a flaw in the bending position 230a or the like of the pipe line 230, as shown, for example, in FIG. 26, when the bending operation knob 213 is operated to bend the bendable part 211, the EC coil 220a and the inner periphery of the pipe line 230 will contact with each other and the EC coil 220b and the inner periphery of the pipe line 230 will contact with each other so that, in the same manner, the position of the inner periphery of the pipe line 230 in which a flaw is to be detected by the EC coils 220a and 220b will be in a fixed direction. Further, a flaw can be detected while the EC coil 220a is moved along the inner periphery of the bending part 230a of the pipe line 230.

In case the inside diameter of the pipe line 230 is different or the numbers of windings of the EC coils 220a and 220b are to be varied, the EC coils 220a and 220b will be able to be easily replaced and the fitting positions of the EC coils 220a and 220b will be able to be easily determined. Other flaw detection sensing members can be used instead of the EC coils 220a and 220b.

Also, a supporting member of the same contour formed, for example, of a synthetic resin may be used instead of one of the EC coils 220a and 220b.

That is, according to this embodiment, there are effects that the playing part within the pipe line 230 on the tip side of the tip part 210, bendable part 211 and flexible tube part 212, that is, on the tip side of the insertable part 207 can be controlled by the contact of the interior of the pipe line with the EC coils 220a and 220b or tip part 210 by the bending of the bendable part 210, the EC coils 220a and 220b can be stabilized within the pipe line 230 and the depth or position of the flaw can be accurately obtained.

The other formations, operations and effects are the same as in the first embodiment.

Figure 27:
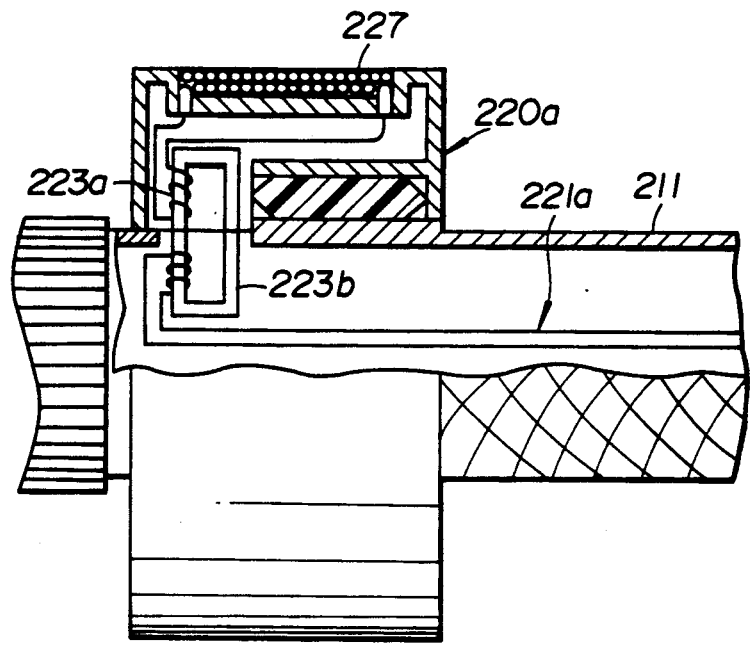
FIG. 27 is an explanatory view of a bendable part of an endoscope relating to the eighth embodiment of the present invention.

In FIG. 27 is shown the eighth embodiment of the present invention. The same components as in the seventh embodiment shall bear the same reference numerals and shall not be explained here.

The bendable part 211 of the endoscope is provided with an iron core 223b on which an EC signal line 221a is wound like a coil.

The EC coil 220a is provided with an iron core 223a so as to lead to the iron core 223b. A signal line connected to a detecting coil 227 detecting the position and size of a flaw or the like by an eddy current loss is wound like a coil on the iron core 223a.

A transformer may be made of the iron cores 223a and 223b.

As formed like this, there are effects that the signal lines of the EC coil 220a and endoscope apparatus can be connected with each other by the lead of the iron cores 223a and 223b, noise by the contact can be prevented and water-tightness of the bendable part can be elevated.

The other formations, operations and effects are the same as in the seventh embodiment.

Figure 28:
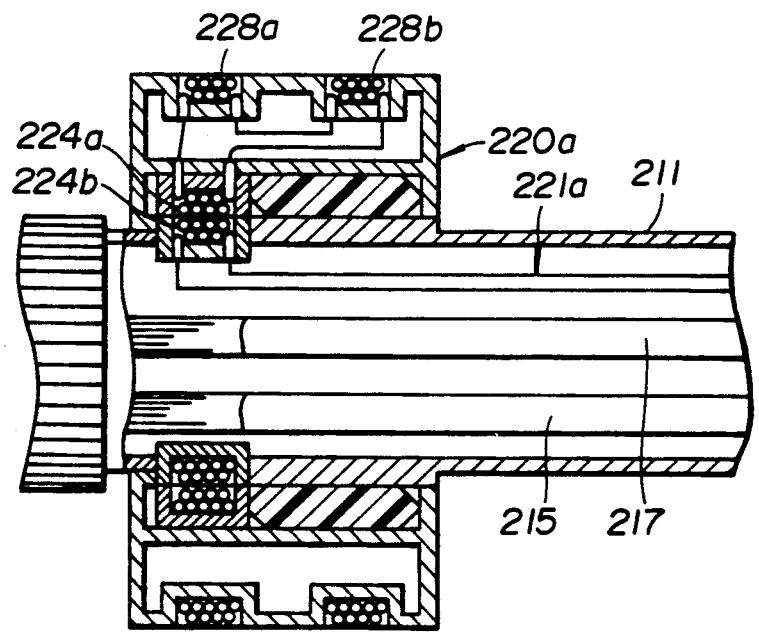
FIG. 28 is an explanatory view of a bendable part of an endoscope relating to the ninth embodiment of the present invention.

In FIG. 28 is shown the ninth embodiment of the present invention. The same components as in the seventh or eighth embodiment shall bear the same reference numerals and shall not be explained here.

The bendable part 211 of the endoscope is internally provided with a light guide 215, an image guide 217 leading an image of an inspected object to an eyepiece part connected to the operating part (not illustrated) at the rear end from the tip part and an EC signal line 221a and is provided on the outer peripheral surface with a coil 224b to which the EC signal line 221a is connected.

The EC coil 220a is provided on the inside diameter surface with a coil 224a so as to lead to the coil 224b. A signal line connected to detecting coils 228a and 228b detecting the position and size of a flaw or the like by an eddy current loss is connected to the coil 224a.

The detecting coils 228a and 228b are different in the coil winding direction so as to be of a self-comparing type.

A ring-like transformer may be made of the coils 224a and 224b.

As formed like this, there are effects that the signal lines of the EC coil 220a and endoscope apparatus can be connected with each other by the lead of the coils 224a and 224b, the ring-like transformer by the coils 224a and 224b is small in contour and the bendable part 211 and EC coil 220a can be made small in diameter.

The other formations, operations and effects are the same as in the seventh and eighth embodiments.

The flaw detection sensing member may be to detect a flaw, for example, by ultrasonic waves.

Also, the tip part may be an optical adapter provided internally with a solid state imaging device or the like.

The flaw detection sensing member may be secured to or integrated with the bendable part.

In FIGS. 29 to 32 is shown the tenth embodiment of the present invention.

Figure 30:
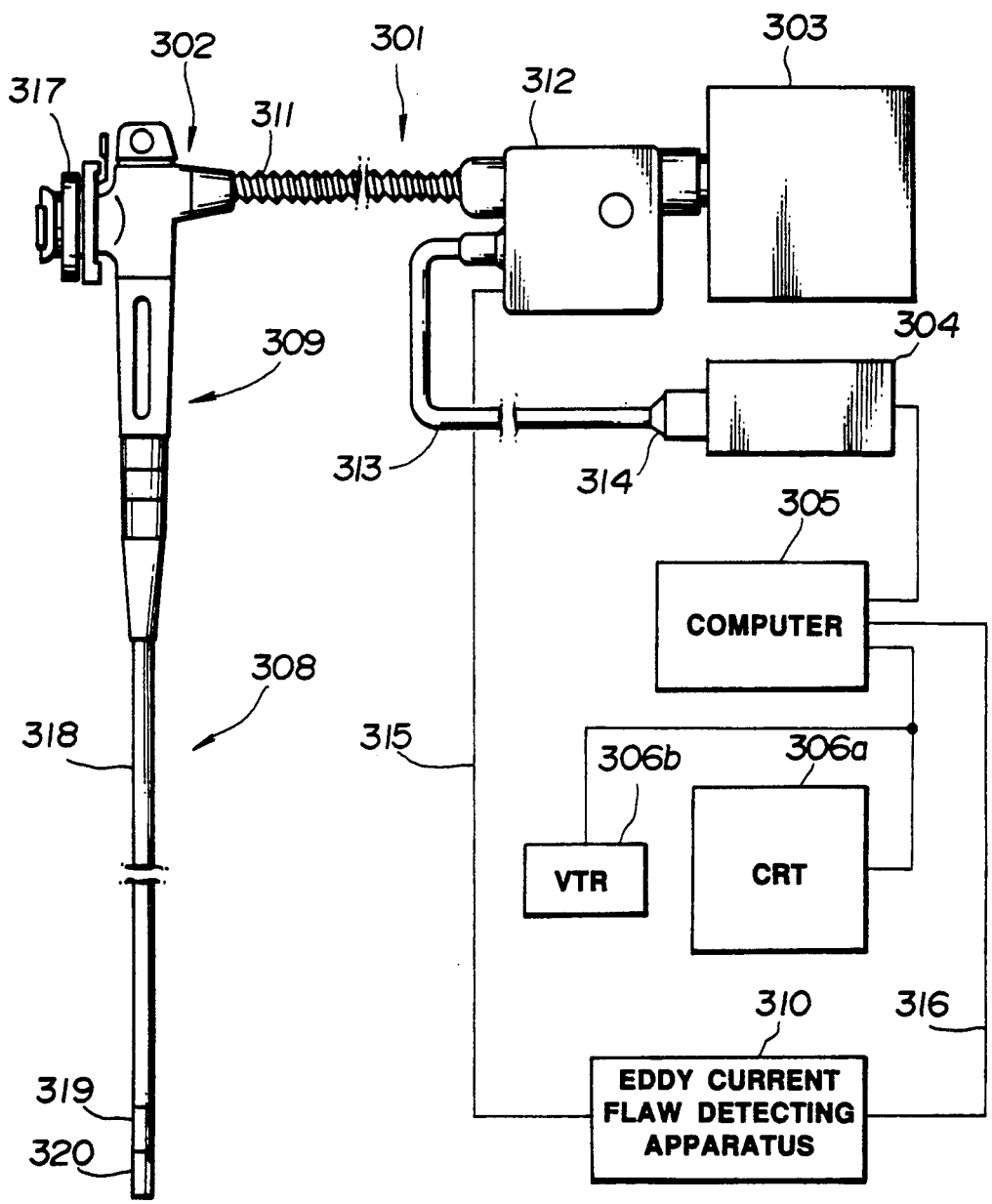

As shown in FIG. 30, an endoscope apparatus 301 comprises an endoscope 302, a power source apparatus 303 connected to the endoscope 302, a camera controlling unit (abbreviated as a CCU hereinafter) 304, an eddy current flaw detecting apparatus 310, a computer 305 connected to the CCU and eddy current flaw detecting output from the apparatus 310, a CRT 306a inputting an image signal computer 305 and displaying an image and a VTR 306b inputting an image signal output from the computer 305 and recording an image.

The endoscope 302 is provided with an elongate flexible insertable part 308 and a thick operating part 309 connected to the insertable part 308 at the rear end. A flexible universal cord 311 is extended sidewise from the operating part 309 and is provided at the end with a power source connector 312 to be connected to the power source apparatus 303. A CCU cable 313 is extended from the power source connector 312 and is provided at the end with a CCU connector 314 to be connected to the CCU 304. The power source connector 312 and eddy current flaw detecting apparatus 310 are connected with each other through a cable 315. The eddy current flaw detecting apparatus 310 and computer 305 are connected with each other through a cable 316.

The insertable part 308 is formed by successively providing a bendable part 319 and rigid tip part 320 at the tip of a soft part 318 on the operating part 309 side. The operating part 309 is provided with a bending operation knob 317 bending the bendable part 319, for example, vertically/horizontally.

Figure 29:
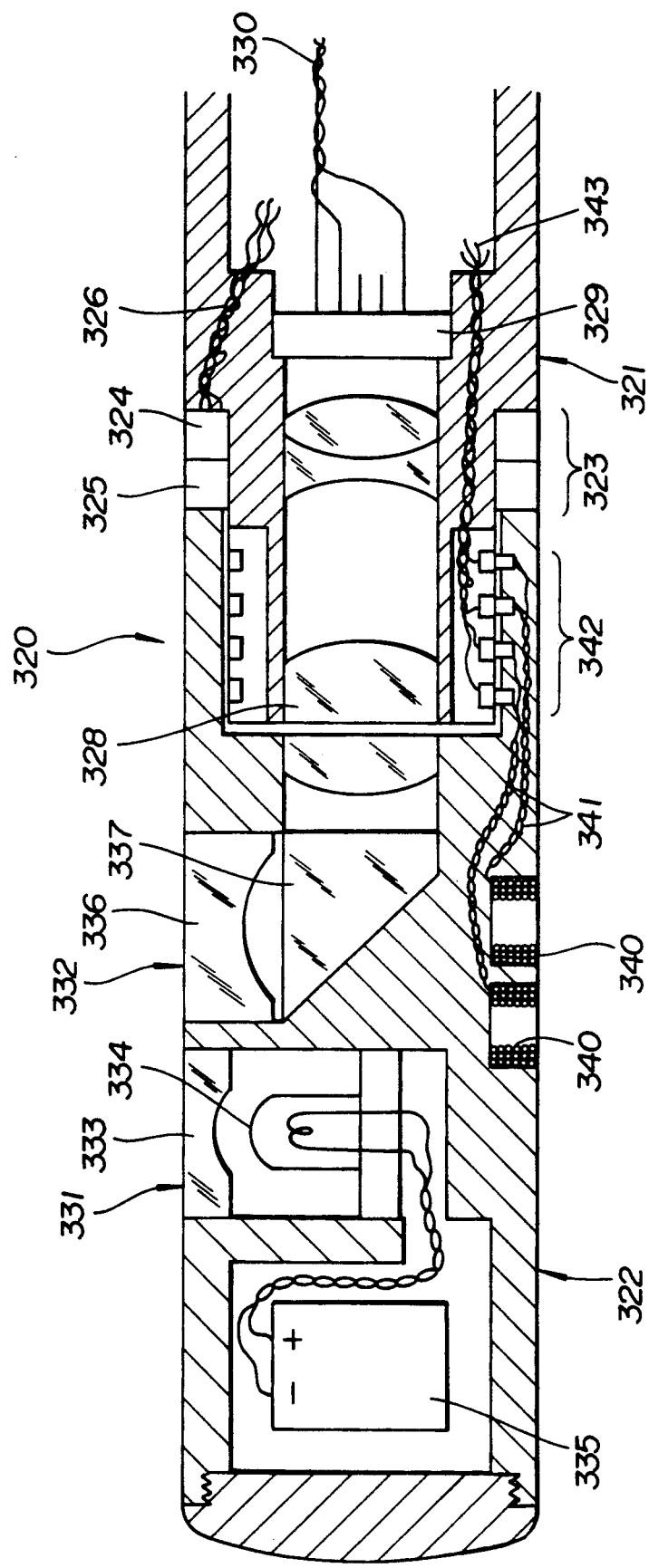
FIGS. 29 to 32 relate to the tenth embodiment of the present invention.

As shown in FIG. 29, the tip part 320 is provided with a tip part body 321 and a rotary part 322 provided on the tip side of the tip part body 321. The rotary part 322 is fitted to the tip body 321 through an ultrasonic motor 323 rotatably with the axial direction of the insertable part 308 as a center. The ultrasonic motor 323 has a stator 324 provided on the tip part body 321 and a rotor 325 provided on the rotary part 322 side and opposed to the stator 324 to which a signal line 326 is connected. The signal line 326 is to be connected to the power source apparatus 303 through the insertable part 308, operating part 309, universal cord 311 and power source connector 312.

Within the tip part body 321, an image forming optical system 328 is provided and a solid state imaging device which is, for example, a CCD 329 is arranged in the image forming position of the image forming optical system 328. A signal line 330 connected to the CCD 329 is inserted through the insertable part 308, operating part 309, universal cord 311, power source connector 312 and CCU cable 313 and is connected to the CCU connector 314.

On the other hand, an illuminating window 331 and observing window 332 are provided in the order mentioned from the tip side on one side surface of the rotary part 322. The illuminating window 331 is fitted with a light distributing lens 333 inside which an illuminating lamp 334 is arranged. A battery 335 provided within the rotary part 322 is connected to the lamp 334. The observing window 332 is fitted with a objective lens 336 inside which is arranged a prism 337 leading a light from the objective lens 336 to the image forming optical system 328 within the tip part body 321.

In the side part of the rotary part 322 on the side opposite the illuminating window 331 and observing window 332, a plurality or two in FIG. 29 of eddy current flaw detecting coils (mentioned as EC coils hereinafter) 340 are provided in the axial direction of the insertable part 308. A signal line 341 connected to the EC coil 340 is connected to a signal line 343 on the tip part body 321 side through a slip ring 342 provided between the rotary part 322 and tip part body 321. The signal line 343 is to be connected to the eddy current flaw detecting apparatus 310 through the insertable part 308, operating part 309, universal cord 311, power source connector 312 and cable 315.

The formations of the eddy current flaw detecting apparatus 310 and computer 305 shall be explained in the following with reference to FIG. 31.

The eddy current flaw detecting apparatus 31 is provided with as many oscillators 345 as EC coils 340. Bridges 346 are connected respectively to the plurality of the oscillators 345. As shown in FIG. 32, the bridge 346 comprises four devices of impedances Za, Zb, Zc and Zd and the device corresponding to one of them, for example, to the impedance Za is the EC coil 340. The bridge 346 is usually balanced. When there is a flaw or the like in the object being inspected, the impedance of the EC coil 340 will vary, the balance of the bridge 346 will be broken and an output voltage will be obtained from both ends of the impedance ZG provided on the diagonal. Returning to FIG. 31, the respective outputs of the oscillators 345 are applied to the respective input ends of a switching switch 347 having a plurality of input ends and one output end. The respective outputs of the bridges 346 are applied to the respective input ends of a switching switch 348 having a plurality of input ends and one output end. The output end of the switching switch 348 is connected to the input end of an amplifier 349. The output end of the amplifier 349 and the output end of the switching switch 347 are connected to a synchronous detector 350. The output of the synchronous detector 350 is input into an A/D converter 351 of a computer 305. The output of the A/D converter 351 is input into a CPU 352. The output of the CPU 352 is stored in a frame memory 353 in which a video signal from the CCU 304 is also to be stored. The output of the frame memory 353 is to be input into the CRT 306a and VTR 306b. By the CPU 352, the switching switches 347 and 348 are switched and the VTR 306 is turned on/off.

The operation of this embodiment shall be explained in the following.

When the insertable part 308 of the endoscope 302 is inserted into an object to be inspected such as, for example, a pipe and the inside surface of the pipe is illuminated with the illuminating lamp 334, an optical image of the inside surface of the pipe formed by the prism 37 and image forming optical system 328 will be imaged by the CCD 329. The output signal of the CCD 329 will be input into the CCU 304 through the signal line 330 and will be made into a video signal. The video signal will be stored in the frame memory within the computer 305.

An alternating driving current will be input from the plurality of oscillators 345 within the eddy current flaw detecting apparatus 310 to the plurality of bridges 346 including the plurality of EC coils 340 provided in the tip part 320 of the insertable part 308 of the endoscope 302. Thereby, alternating magnetic fields will be generated from the EC coils 340 and an eddy current will be generated within the pipe of a conductor. The bridges 346 are balanced in such a place where there is no flaw as the inside surface of the pipe in advance before the inspection. If there is a flaw in the pipe during the inspection, the eddy current will vary and the impedance of the EC coil 340 will vary. Then, the balance of the bridges 346 will be broken and outputs will come out of the bridges 346. Each of the EC coils 340 is provided with the oscillator 345 and bridge 346 so as to independently make an eddy current flaw detection.

The outputs from the plurality of oscillators 345 and the outputs from the plurality of bridges 346 will be selected respectively by the switching switches 347 and 348. The switching switches 347 and 348 will select the respective outputs of the pairs of the oscillators 345 and brides 346. The outputs of the bridges 346 selected by the switching switch 348 will be amplified by the amplifier 349 and will be input into the synchronous detector 350. Also, the outputs of the oscillators 345 selected by the switching switch 347 will be input into the synchronous detector 350. In the synchronous detector 350 in which the phases of the output waveforms of the oscillators 345 and of the output waveforms of the bridges 346 will be compared and a direct current output corresponding to the phase difference of both will be obtained.

The output of the synchronous detector 350 will be input into the computer 305 and will be converted into a digital signal by the A/D converter 351 within the computer 305. The digital signal will be operated as required by the CPU 532 and will be stored into the frame memory 353. The video signal from the CCU 304 and the output of the CPU 352 will be synthesized in the frame memory 353, will be displayed on the CRT 306a by the displaying circuit 354 and will be recorded in the VTR 306b. That is, the optical image of the inside surface of the pipe and the detected information of the flaw will be synthesized, will be displayed on the CRT 306a and will be recorded on the VTR.

The observation and eddy current flaw detection may be made while rotating the rotary part 322 with the ultrasonic motor 323 and, as required, for example, when a flaw is detected, the rotary part 322 may be rotated by 180 degrees to confirm the flaw.

Thus, in this embodiment, a plurality of EC coils 340 for detecting a flaw independently of each other are provided in the tip part 320 of the insertable part 308 of the endoscope 302 so that an eddy current flaw detection may be possible in a plurality of places without changing the position of the insertable part 308 of the endoscope 302. The inspecting speed, that is, the endoscope inserting speed may be made higher than ever and the inspecting time may be greatly reduced.

Figure 31:
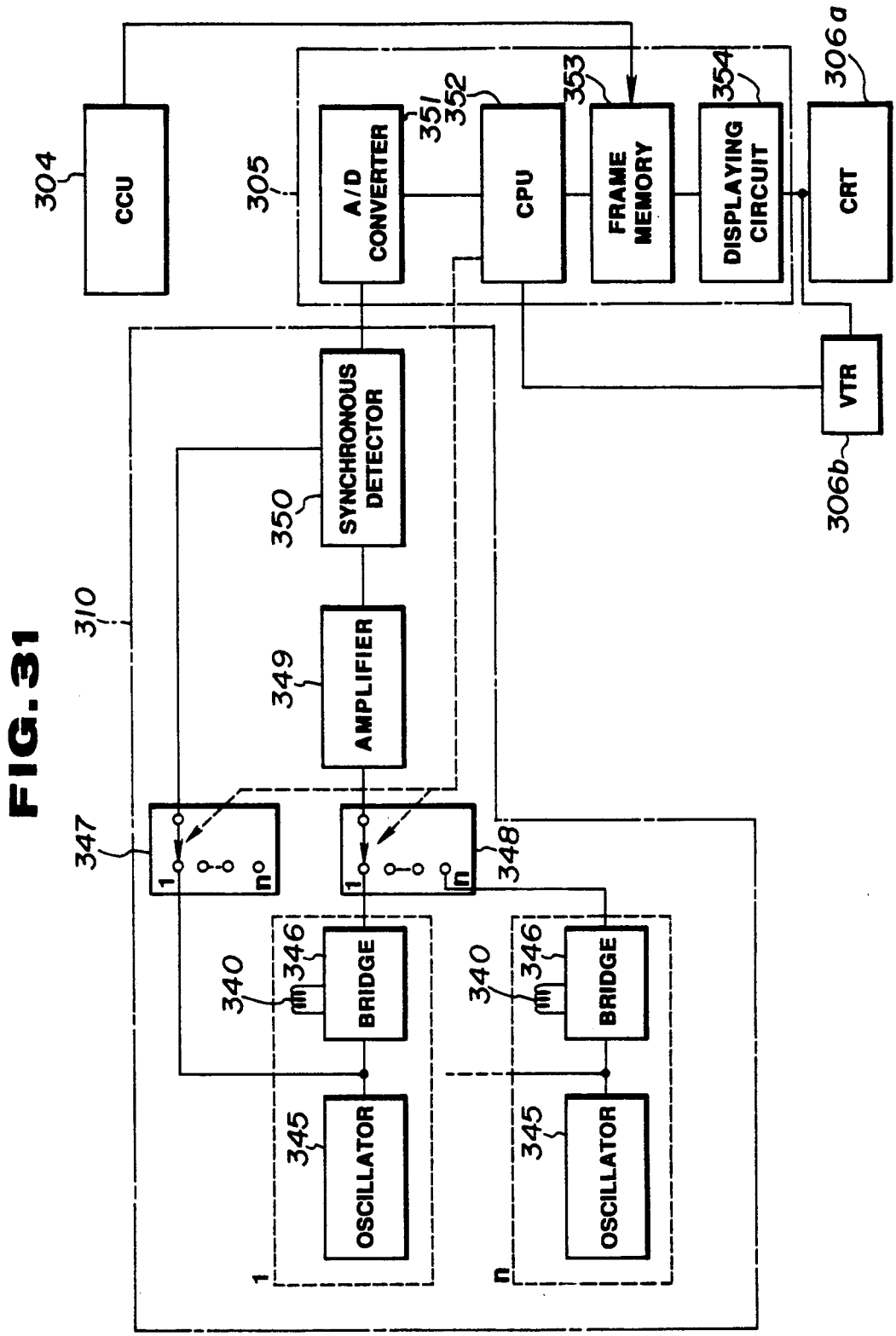
Figure 32:
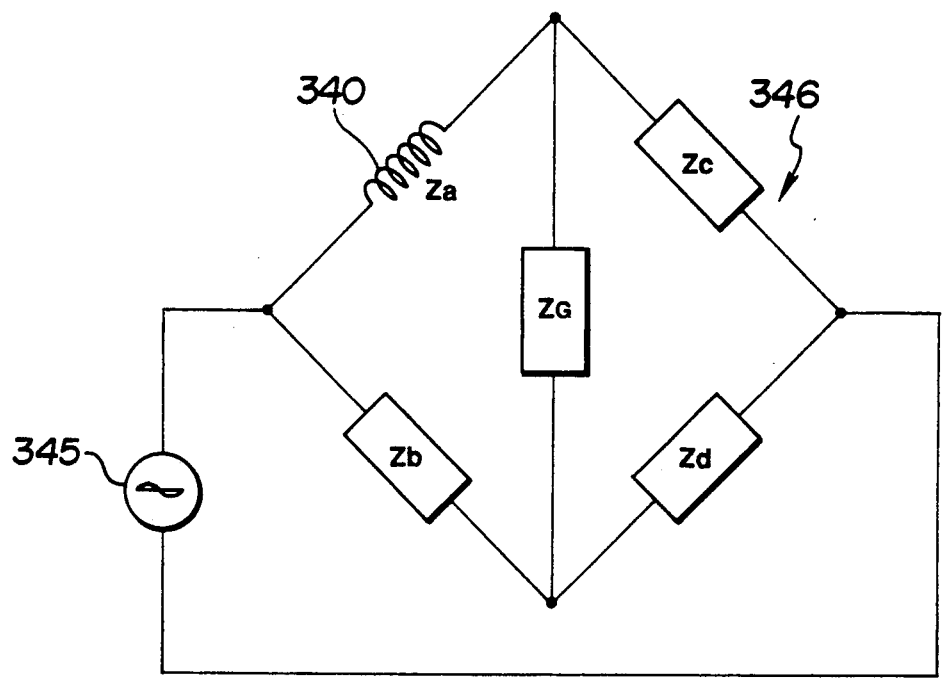

For example, the amplifier 349 and synchronous detector 350 explained in FIG. 31 may be provided for each EC coil 340.

The other formations, operations and effects are the same as in the fifth embodiment.

Figure 33:
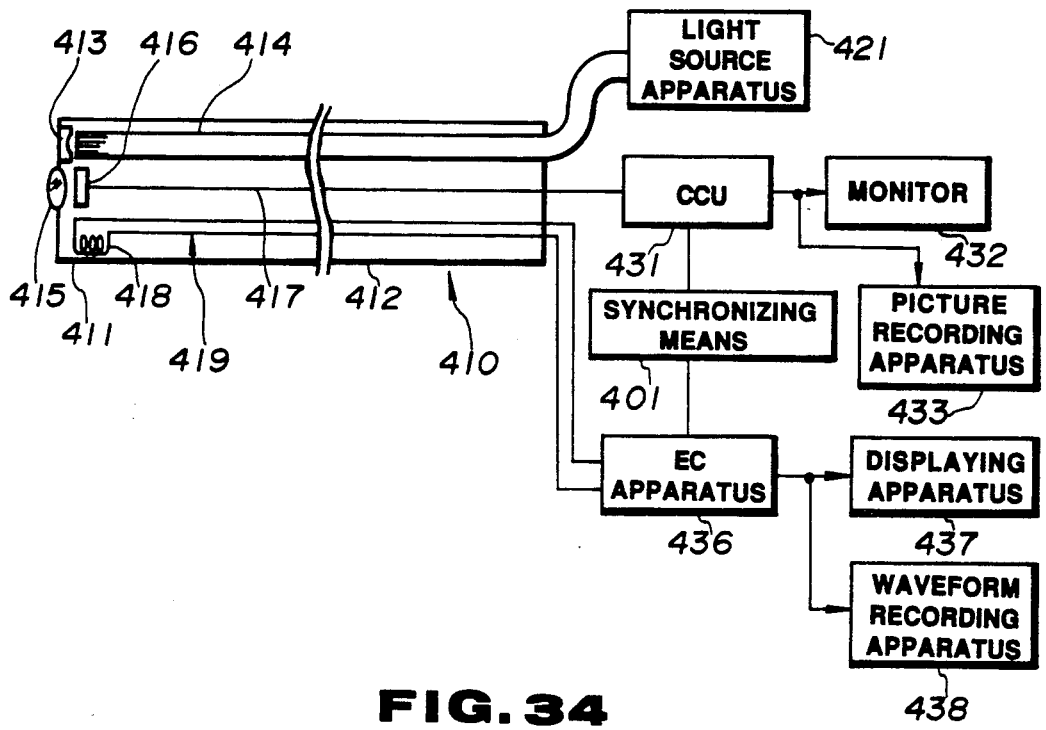
Figure 34:
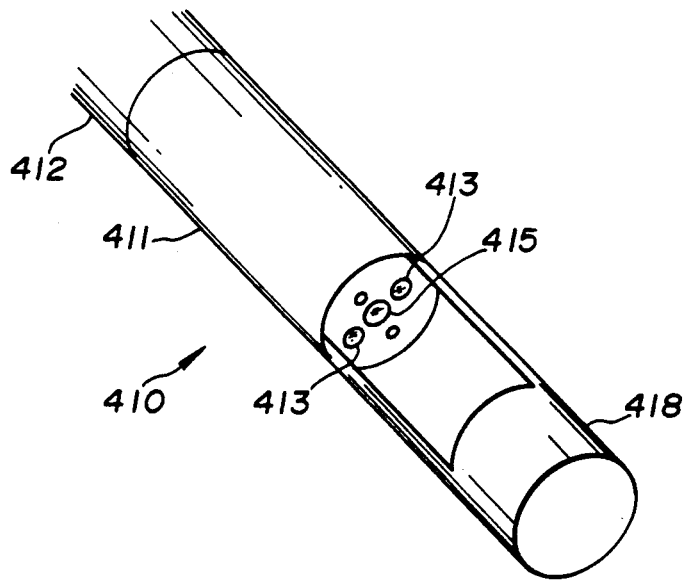

In FIGS. 33 to 35 is shown the 11th embodiment of the present invention.

As shown in FIG. 33, the flaw detecting endoscope apparatus comprises an endoscope 410 to be inserted into an object to be inspected such as a pipe line. A light source apparatus 421 feeds an illuminating light to the endoscope 410. A camera controlling unit (mentioned as a CCU hereinafter) 431 drives a CCD (charge coupled device) which is a later described solid state imaging device provided within the endoscope 410, obtaining an imaging signal from the CCD and converting the imaging signal to a standard video signal. A monitor displays the standard video signal. An image recording apparatus 433 which is, for example, a VTR apparatus records the standard video signal by the control of the CCU 431. A flaw detecting apparatus (mentioned as an EC apparatus hereinafter) drives a later described flaw detecting coil provided at the tip of the endoscope 410, detecting a flaw or the like electrically by a signal from the flaw detecting coil and making it possible to display the flaw or the like in a later described displaying apparatus. A displaying apparatus 437 displays the detecting signal from the EC apparatus 436, for example, as a video image. A waveform recording apparatus 438 records the detecting signal from the EC apparatus 436, for example, on a recording sheet. A synchronizing means 401 connects the CCU 431 and EC apparatus 436 with each other, synchronizing the CCU 431 and EC apparatus 436 and controlling the CCU 431 and EC apparatus 436.

As shown in FIGS. 33 and 34, the endoscope 410 comprises an elongate insertable part 412 and a tip part 411 provided at the tip of the insertable part 412.

An illuminating optical system 413 and objective optical system 415 are arranged on the tip surface of the tip part 411. An eddy current flaw detecting coil (mentioned as an EC coil hereinafter) 418, for detecting a flaw or the like with an eddy current, is provided in the axial direction of this tip surface.

As shown in FIG. 33, the endoscope 410 is internally provided with a light guide 414 having the exit end surface arranged on the rear surface of the illuminating optical system 413 and leading the illuminating light. A solid state imaging device is arranged on the image forming surface of the objective optical system 415 as, for example, a CCD 416. An imaging signal line 417 is connected to the CCD 416. A flaw detecting signal line 419 is connected to the EC coil 418.

The above mentioned light guide 414 is to be connected to the light source apparatus 421.

The CCU 431 is to be connected with the CCD 416 through the imaging signal line 417, the synchronizing means 401, monitor 432 and image recording apparatus 433.

The EC apparatus 436 is to be connected with the EC coil 418 through the flaw detecting signal line 419, the synchronizing means 401, displaying apparatus 437 and waveform recording apparatus 438.

The illuminating light from the light source apparatus 421 will be input through the light guide 414 and will be radiated to an object to be inspected (not illustrated) or the like from the tip part 411.

The image of the object or the like radiated by the illuminating light as described above will be formed on the photoelectric converting surface of the CCD 416 by the objective optical system 415 and will be a photoelectrically converted to be an imaging signal which will be input into the CCU 431.

The imaging signal input into the CCU 431 will be converted to a standard video signal by the CCU 431 and will be output to the monitor 432 and image recording apparatus 433.

The EC apparatus 436 will drive the EC coil 418, will process the variation of the signal by the EC coil 418 and will output the signal to the displaying apparatus 437 so as to be displayed and to the waveform recording apparatus 438 so as to be recorded.

The synchronizing means 401 will synchronize the imaging timing of the CCU 431 and the flaw detecting timing of the EC apparatus 436.

The operation of the thus formed flaw detecting endoscope apparatus shall be explained.

As shown in FIG. 35(A), by the fall of the horizontal synchronizing signal of the CCU 431, the synchronizing means 401 will output to the EC apparatus 436 a control signal to drive the EC coil 418 to make a flaw detecting process.

By the rise of the horizontal synchronizing signal of the CCU 431, the synchronizing means 401 will output to the EC apparatus 436 a control signal to stop the drive of the EC coil 418, that is, to stop the flaw detecting process.

Therefore, as shown in FIG. 35(C), by the control signal of the synchronizing means 401, the EC apparatus 436 will be controlled to drive or stop the EC coil 418, that is, to make or stop the flaw detecting process.

In case the EC apparatus 436 is controlled from the synchronizing means 401 to make a flaw detecting process, the EC apparatus 436 will drive the EC coil 418, will process the variation of the signal by the EC coil 418 shown in FIG. 35(E) and will output the signal to the displaying apparatus 437 so as to be displayed and to the waveform recording apparatus 438 so as to be recorded.

The displaying apparatus 437 will display, for example, on a picture the signal from the EC apparatus 436. The waveform recording apparatus 438 will record, for example, on a recording sheet the signal from the EC apparatus 436.

In the period other than during the horizontal synchronizing signal, that is, in the period when the control signal of the synchronizing means 401 is not being output to the EC apparatus 436, the CCU 431 will drive the CCD 416, will obtain an imaging signal from the CCD 416, will convert the imaging signal to a standard video signal and will output it to the monitor 432 and image recording apparatus 433.

That is, there are effects that, in the period when the CCU 431 obtains the imaging signal from the CCD 416, the EC apparatus 436 will not drive the EC coil 418, the driving signal to the EC coil 418 will be prevented from being superimposed as noise on the driving signal to the CCD 416. The imaging signal from the CCD 416 and the driving signal to the CCD 416 and the imaging signal from the CCD 416 will not be superimposed as noise on the signals of the EC apparatus 436 and EC coil 418.

The flaw detecting means for detecting a flaw or the like is not limited to be the EC apparatus but may be a non-destroying flaw detecting apparatus using, for example, ultrasonic waves.

As explained above, according to the present invention, as the operation of the endoscope is controlled by a flaw sensing signal from an eddy current flaw detecting apparatus, in case only the image required for the inspection is to be recorded, it will be able to be recorded without making an operation for the recording, the inspection time can be reduced and the inspection can be efficiently made.

Also, there are effects that, by a flaw detection sensing member or supporting member, the flaw detection sensing member within a pipe line can be stabilized in the flaw detecting position and the precision of detecting the position and size of the flaw by the flaw detecting inspection can be elevated.

There is also an effect that, as a plurality of detecting parts for detecting flaws independently of each other are provided, the eddy current flaw detecting inspection time can be reduced.

Also, there are effects that a clear endoscope image can be obtained without any interference and obstruction of the endoscope observed image and eddy current flaw detecting signal with each other and a flaw or the like of an object being inspected can be positively detected.

It is apparent that, in this invention, a wide range of different working modes can be formed based on the invention without deviating from the spirit and scope of the invention. This invention is not restricted by its specific working modes except being limited by the appended claims.

What is claimed is:

1. An eddy current flaw detecting endoscope apparatus comprising:

an endoscope having an elongate insertable part and an objective optical system provided on a tip side of said insertable part;

an eddy current flaw detecting means for detecting a flaw in an inside of a pipe which is being inspected and for generating a flaw detecting signal, said eddy current flaw detecting means having a) a flaw detecting mean provided on the tip side of said endoscope and b) a signal processing means, connected to said flaw detecting means, for processing a signal from said flaw detecting means; and a controlling means, connected to said eddy current flaw detecting means, for generating a control signal which controls, based on said flaw detecting signal from said eddy current flaw detecting means, operation of a picture image recording means.

2. An eddy current flaw detecting endoscope apparatus comprising:

an endoscope having an elongate insertable part and an objective optical system provided on a tip side of said insertable part;

a video signal processing apparatus, connected to said endoscope, said video signal processing apparatus having an imaging means for photoelectrically converting an optical image from said objective optical system, said video signal processing apparatus a) processing a signal from said imaging means to convert said signal into a standard video signal and b) generating a predetermined timing signal;

an eddy current flaw detecting means for detecting a flaw in an inside of a pipe under inspection and for generating a flaw detecting signal, said eddy current flaw detecting means having a) at least one flaw detecting means provided in said insertable part and b) a signal processing means, connected to said at least one flaw detecting means, for processing a signal from said at least one flaw detecting means; and a controlling means, connected to said eddy current flaw detecting means and said video signal processing apparatus, for controlling when said eddy current flaw detecting means operates based upon said timing signal from said video signal processing apparatus.

3. An eddy current flaw detecting endoscope apparatus according to claim 1 further comprising a tip optical adapter to be removably fitted to a tip part of said endoscope, said objective optical system further having a connecting means to be removably fitted to said tip optical adapter.

4. An eddy current flaw detecting endoscope apparatus according to claim 1 further comprising a tip optical adapter to be removably fitted to a tip part of said endoscope, said objective optical system being provided in said tip optical adapter.

5. An eddy current flaw detecting endoscope apparatus according to claim 1 wherein said insertable part of said endoscope has a bendable part and a flexible tube part connected to said bendable part at a rear end, said flaw detecting means is provided within said flexible tube part near said bendable part and said eddy current flaw detecting means further has a signal transmitting means provided within said endoscope and electrically connecting said flaw detecting means and signal processing means with each other.

6. An eddy current flaw detecting endoscope apparatus according to claim 1 wherein said insertable part has a bendable part near the tip side and said flaw detecting means has a connecting means to be removably fitted to said bendable part on an outer peripheral surface of at least one of the front end and rear end.

7. An eddy current flaw detecting endoscope apparatus according to claim 1 wherein said insertable part of said endoscope has a tip side part at the tip and said eddy current flaw detecting means is arranged in said tip part.

8. An eddy current flaw detecting endoscope apparatus according to claim 1 further comprising a visual field angle converting adapter having a rotary mirror converting a visual field direction of said objective optical system and a motor rotating and driving said rotary mirror, said flaw detecting means being provided in said visual field angle converting adapter.

9. An eddy current flaw detecting endoscope apparatus according to claim 6 further comprising a pseudo member of the same shape as of the above mentioned eddy current flaw detecting means.

10. An eddy current flaw detecting endoscope apparatus according to claim 3 or 6 wherein said flaw detecting means further has a signal connecting means to be connected electrically with said endoscope.

11. An eddy current flaw detecting endoscope apparatus according to claim 3, 4 or 6 wherein said eddy current flaw detecting means further has a signal transmitting means provided within said endoscope and electrically connecting said flaw detecting means and signal processing means with each other and said signal transmitting means has a signal connecting means connecting electrically removably.

12. An eddy current flaw detecting endoscope apparatus according to claim 7 wherein the tip part of said endoscope has a tip part body, a rotary part and an oscillating wave motor rotating and driving said rotary part with respect to said tip part body.

13. An eddy current flaw detecting endoscope apparatus according to claim 12 wherein said eddy current flaw detecting means is provided in said rotary part, said eddy current flaw detecting means further comprising a signal transmitting means electrically connecting said flaw detecting means and signal processing means with each other, said endoscope is internally provided with said signal transmitting means and said tip part body and rotary part have contacts electrically connecting said signal transmitting means.

14. An eddy current flaw detecting endoscope apparatus according to claim 11 wherein said signal connecting means consists of contacts connected by contact.

15. An eddy current flaw detecting endoscope apparatus according to claim 11 wherein said signal connecting means is a magnetic induction means connecting by magnetic induction.

16. An eddy current flaw detecting endoscope apparatus according to claim 15 wherein said magnetic induction means includes iron cores and coils.

17. An eddy current flaw detecting endoscope apparatus according to claim 15 wherein said magnetic induction means includes a ring-like transformer.

18. An eddy current flaw detecting endoscope apparatus according to claim 1 wherein said endoscope has a tip part at the tip side of said insertable part, said tip part is internally provided with an imaging means for photoelectrically converting an optical image based on said objective optical system and said eddy current flaw detecting endoscope apparatus further provided with 1) an image signal processing apparatus for processing a signal for said imaging means to convert said signal to a standard video signal and 2) said picture image recording means for recording said standard video signal of said image signal processing apparatus.

19. An eddy current flaw detecting endoscope apparatus according to claim 18 wherein said picture image recording means is a video tape recorder apparatus.

20. An eddy current flaw detecting endoscope apparatus according to claim 1 wherein said signal processing means has at least one bridge circuit detecting a variation of an impedance of said flaw detecting means, at least one oscillating means feeding a signal to said bridge circuit and at least one detecting means synchronizing and detecting a signal of said bridge circuit and a signal of said oscillating means and generating said flaw detecting signal.

21. An eddy current flaw detecting endoscope apparatus according to claim 20 wherein said signal processing means further has a phase shifting means for varying a phase of the signal of said oscillating means and outputting said phase to said detecting means.

22. An eddy current flaw detecting endoscope apparatus according to claim 18 wherein said controlling means includes a trigger circuit generating a control signal controlling a recording operation and recording stopping operation of said picture image recording means with said flaw detecting signal of said eddy current flaw detecting apparatus.

23. An eddy current flaw detecting endoscope apparatus according to claim 18 wherein said controlling means is a computer generating a control signal controlling recording and recording stopping operation of said picture image recording means with said flaw detecting signal of said eddy current flaw detecting means and said computer has at least one A/D converting circuit and a CPU.

24. An eddy current flaw detecting endoscope apparatus according to claim 23 wherein said computer further has a frame memory superimposing said flaw detecting signal from said eddy current flaw detecting means on said standard video signal from said image signal processing apparatus.

25. An eddy current flaw detecting endoscope apparatus according to claim 24 wherein said CPU and frame memory further enhance an outline of a part corresponding to a flaw of said standard video signal from said image signal processing apparatus.

26. An eddy current flaw detecting endoscope apparatus according to claim 1 further comprising an inserting means for automatically inserting said part of said endoscope through said inside of said pipe being inspected and a speed controlling means for controlling the inserting speed of said inserting means.

27. An eddy current flaw detecting endoscope apparatus according to claim 26 wherein said speed controlling means includes a CPU.

28. An eddy current flaw detecting endoscope apparatus according to claim 20 wherein said eddy current flaw detecting means further has a first switching means for switching a plurality of said oscillating means and detecting means, a second switching means for switching a plurality of said bridge circuits and detecting means and a switching controlling means for controlling said first switching means and second switching means.

29. An eddy current flaw detecting endoscope apparatus according to claim 28 wherein said switching controlling means includes a CPU.

30. An eddy current flaw detecting endoscope apparatus according to claim 2 wherein said timing signal is a horizontal synchronizing signal of said standard video signal.

* * * * *